(12) United States Patent
Winter et al.

(10) Patent No.: US 9,758,866 B2
(45) Date of Patent: Sep. 12, 2017

(54) SYNTHESIS AND CHARACTERIZATION OF FIRST ROW TRANSITION METAL COMPLEXES CONTAINING α-IMINO ALKOXIDES AS PRECURSORS FOR DEPOSITION OF METAL FILMS

(71) Applicant: Wayne State University, Detroit, MI (US)

(72) Inventors: Charles H. Winter, Bloomfield Hills, MI (US); Lakmal C. Kalutarage, Detroit, MI (US)

(73) Assignee: Wayne State University, Detroit, MI (US)

( * ) Notice: Subject to any disclaimer, the term of this patent is extended or adjusted under 35 U.S.C. 154(b) by 658 days.

(21) Appl. No.: 13/765,981

(22) Filed: Feb. 13, 2013

(65) Prior Publication Data
US 2014/0227444 A1  Aug. 14, 2014

(51) Int. Cl.
*C23C 16/18* (2006.01)
*C23C 16/02* (2006.01)
(Continued)

(52) U.S. Cl.
CPC .............. *C23C 16/18* (2013.01); *C07F 1/005* (2013.01); *C07F 11/005* (2013.01);
(Continued)

(58) Field of Classification Search
CPC ...... C07F 1/005; C07F 11/005; C07F 13/005; C07F 15/025; C07F 15/045; C07F 15/065; C23C 16/18
See application file for complete search history.

(56) References Cited

U.S. PATENT DOCUMENTS 3,562,308 A   2/1971  Costa et al.
5,721,014 A   2/1998  Fakler et al.
(Continued)

FOREIGN PATENT DOCUMENTS

KR   10-2010-0061183 A   6/2010
WO      2012027357 A2    3/2012
(Continued)

OTHER PUBLICATIONS

Elam (ECS Transactions, 3 (15) 271-278 (2007)).*
(Continued)

*Primary Examiner* — Joel Horning
(74) *Attorney, Agent, or Firm* — Brooks Kushman P.C.

(57) ABSTRACT

A compound that is useful for forming a metal by reaction with a reducing agent is described by formula (I):

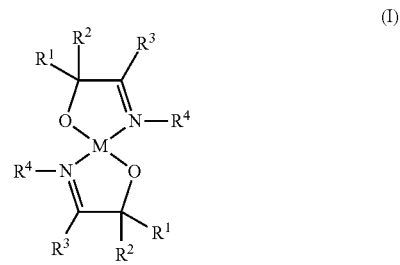

wherein
M is a metal selected from Groups 2 through 12 of the Periodic Table; and
$R^1$, $R^2$, $R^3$, and $R^4$ are each independently H or $C_1$-$C_8$ alkyl.

18 Claims, 25 Drawing Sheets

(51) Int. Cl.
  *C23C 16/455* (2006.01)
  *C07F 11/00* (2006.01)
  *C07F 13/00* (2006.01)
  *C07F 15/02* (2006.01)
  *C07F 15/04* (2006.01)
  *C07F 15/06* (2006.01)
  *C07F 1/00* (2006.01)

(52) U.S. Cl.
  CPC .......... *C07F 13/005* (2013.01); *C07F 15/025* (2013.01); *C07F 15/045* (2013.01); *C07F 15/065* (2013.01); *C23C 16/02* (2013.01); *C23C 16/45553* (2013.01)

(56) References Cited

U.S. PATENT DOCUMENTS

| | | | |
|---|---|---|---|
| 6,020,511 | A | 2/2000 | Vaartstra et al. |
| 6,475,276 | B1 | 11/2002 | Elers et al. |
| 6,786,936 | B2 | 9/2004 | Vaartstra |
| 7,632,351 | B2 | 12/2009 | Thompson |
| 2001/0009695 | A1 | 7/2001 | Saanila et al. |
| 2002/0013487 | A1 | 1/2002 | Norman et al. |
| 2002/0098346 | A1 | 7/2002 | Yitzchaik |
| 2005/0097991 | A1 | 5/2005 | Sanjurjo et al. |
| 2005/0186342 | A1 | 8/2005 | Sager et al. |
| 2006/0134331 | A1 | 6/2006 | Thompson |
| 2006/0157863 | A1 | 7/2006 | Marsh |
| 2007/0190248 | A1* | 8/2007 | Elers et al. ............... 427/248.1 |
| 2009/0114874 | A1 | 5/2009 | Norman et al. |
| 2009/0208637 | A1* | 8/2009 | Chen et al. ............... 427/78 |
| 2010/0104755 | A1 | 4/2010 | Dussarrat et al. |
| 2010/0181566 | A1 | 7/2010 | Lee |
| 2012/0058270 | A1 | 3/2012 | Winter et al. |
| 2012/0231579 | A1 | 9/2012 | Quick et al. |
| 2013/0115768 | A1 | 5/2013 | Pore et al. |
| 2013/0251903 | A1 | 9/2013 | Han |

FOREIGN PATENT DOCUMENTS

| | | |
|---|---|---|
| WO | 2012/067439 A2 | 5/2012 |
| WO | 2014077089 A1 | 5/2014 |

OTHER PUBLICATIONS

Non-final Office Action mailed Mar. 23, 2015 in U.S. Appl. No. 13/818,154, filed Feb. 21, 2013, 10 pgs.
English Machine Translation of KR 10-2010-0061183 published Jun. 7, 2010, 31 pgs.
Bart, S.C. et al., "Low-Valent α-Diimine Iron Complexes for Catalytic Olefin Hydrogenation," Organometallics 2005, v. 24, pp. 5518-5527.
d'Alnoncourt, R.N. et al., "The preparation of Cu/Al2O3 catalysts via CVD in a fluidized-bed reactor," Surface and Coatings Technology 201, pp. 9035-904, 2007.
Dieck, H.T. et al., "Reaktionen von Bis(dizadien)eisen(O)," Komplexen. Chem. Ber., 120, pp. 1943-1950, Oct. 2002 (English Abstract).
Gardiner, M.G. et al., "Paramagnetic Bis(1,4-di-tert-butyl-1,4-diazabutadiene) Adducts of Lithium, Magnesium, and Zinc," Inorg. Chem. 1994, 33, pp. 2456-2461.
Ghosh, M. et al., "(α-Diimine)chromium Complexes: Molecular and Electronic Structures; a Combined Experimental and Density Functional Theoretical Study," Inorganic Chem., v. 47, n. 13, (2008), pp. 5963-5970.
Ghosh, M. et al., "A structural, spectroscopic and computational study of the molecular and electronic structure of a [bis(α-diiminato)manganese(II)] π radical complex," Dalton Trans., 2008, pp. 5149-5151.
Gong, Y. et al., "The intra-annular acylamide chelate-coordinated compound: The keto-tautomer of metal (II)-milrinone complex," J. of Molecular Structure 875 (2008), pp. 113-120.

Hassaan, "Mixed ligand complexes of bis(s-methyl-n-arylidene hydrazine carbodithioate) nickel (ii) chelates with some amino acids and nitrogenous heterocycles," J. of Islamic Academy [online] retrieved from http://www.medicaljournal-las.org/3_4Hassaan.pdf on Jul. 1, 2010, pp. 269-272.
Kaltsoyannis, N., "Covalency in metal complexes of 1,4-diazabutadiene (dab). A density functional investigation of the electronic structures of [M(dab)2] (M = Li, Ga or Co) and [Th(NH3)NH2)3(dab)]," J. Chem. Soc., Dalton Trans., 1996, pp. 1583-1589.
Kalutarage, L.C. et al., "Low-Temperature Atomic Layer Deposition of Copper Films Using Borane Dimethylamine as the Reducing Co-reagent," Chem. Mater. 2014, 26, pp. 3731-3738.
Kalutarage, L.C. et al., "Synthesis, Structure, and Solution Reduction Reactions of Volatile and Thermally Stable Mid to Late First Row Transition Metal Complexes Containing Hydrazonate Ligands," Inorg. Chem. 2013, v. 52, pp. 5385-5394.
Kalutarage, L.C. et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films," J. Am. Chem. Soc. 2013, 135, pp. 12588-12591.
Karunarathne, M.C. et al., "Exceptional thermal stability and high volatility in mid to late first row transition metal complexes containing carboyhydrazide ligands," Polyhedron 52 (2013), pp. 820-080.
Khusniyarov, M. M. et al., "Reversible Electron Transfer Coupled to Spin Crossover in an Iron Coordination Salt in the Solid State," Angew. Chem. Int. Ed. 2008, 47, pp. 1228-1231.
Khusniyarov, M.M. et al., "Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino) acenaphthene (BIAN)," Eur. J. Inorg. Chem. 2006, pp. 2985-2996.
Khusniyarov, M.M. et al., "Tuning the Oxidation Level, the Spin State, and the Degree of Electron Delocalization in Horn- and Heteroleptic Bis(α-diimine)iron Complexes," J. Am. Chem. Soc. 2009, v. 131, pp. 1208-1221.
Knisley, T.J. et al., "Low Temperature Growth of High Purity, Low Resistivity Copper Films by Atomic Layer Deposition," Chem. Mater. 2011, v. 23, pp. 4417-4419.
Knisley, T.J. et al., "Volatility and High Thermal Stability in Mid-to Late-First-Row Transition-Metal Dizazdienyl Complexes," Organometallics 2011, v. 30, pp. 5010-5017.
Kreisel, K.A. et al., "Synthesis, Characterization, and Electronic Structure of Diimine Complexes of Chromium," Inorganic Chem., v. 74, n. 12, (2008), pp. 5293-5303.
Kreisel, K.A. et al., "The Shortest Metal-Metal Bond Yet: Molecular and Electronic Structure of a Dinuclear Chromium Diazadiene Complex," J. Am. Chem. Soc. 2007, v. 129, pp. 14162-14163.
Lim, B.S. et al., "Atomic layer deposition of transition metals," Nature Materials, v. 2, Nov. 2003, pp. 749-754.
Mac-Leod-Carey, D.A. et al., "Bix[2-(2,4-dioxopentan-3-ylidene-κO)-1-(4-methoxy-phenyphydrazinato-κN1] copper(II)," Acta Cryst. 2007, E63, pp. m670-m672.
Marten, J. et al., "3-(Arylhydrazono)pentane-2,4-diones and their Complexes with Copper(II) and Nickel(II)—Synthesis and Crystal Structures," Z. Anorg. Allg. Chem. 2005, v. 631, pp. 869-877.
Muresan, N. et al., "Bis(α-diimine)iron Complexes: Electronic Structure Determination by Spectroscopy and Broken Symmetry Density Functional Theoretical Calculations," Inorganic Chem., v. 47, n. 11, (2008), pp. 4579-4590.
Muresan, N. et al., "Bis(α-diimine)nickel Complexes: Molecular and Electronic Structure of Three Members of the Electron-Transfer Series [Ni(L)2]z (z=0, 1+, 2+) (L=2-Phenyl-1,4-bis(isopropyl)-1,4-diazabutadiene). A Combined Experimental and Theoretical Study," Inorganic Chem., v. 46, n. 13, (2007) pp. 5327-5337.
Muresan, N. et al., "Neutral (bis(1,4-diaza-1,3-butadiene)nickel complexes and their corresponding monocations: molecular and electronic structures. A combined experimental and density functional theoretical study," Dalton Trans., 2007, pp. 4390-4398.

(56) References Cited

OTHER PUBLICATIONS

Nassimbeni, L. et al., "The Crystal and Molecular Structure of the Bis-(5-ethyl-5-isoamylbarbiturato)bis(imidazole) Complex of Nickel(II)," Acta Cryst. (1974), B30, p. 2593-2602.
Pangani et al., "Coordination compounds of lanthanides with acetylhydrazine," Inorganica Chimca Acta, v. 94, issues 1-3, Feb. 1984, Abstract p. 79.
Pettinari, C. et al, "Copper and silver derivatives of scorpionates and related ligands," Polyhedron 23 (2004), pp. 451-469.
Popoff, N. et al., "Shifting from Ziegler-Natta to Phillips-Type Catalyst? A Simple and Safe Access to Reduced Titanium Systems for Ethylene Polymerization," Macromol. Rapid Commun. 2011, 32, pp. 1921-1924.
Rijnberg et al., "A Homologous Series of Homoleptic Zinc Bis(1,4-di-tert-butyl-1,4-diaza-1,3-butadiene) Complexes: Kx(Zn(t-BuNCHCHN-t-Bu)2 and (Zn(t-BuNCHCHN-t-Bu)2))(Otf)x (x=1,2)," Inorg. Chem. 1998, v. 37, pp. 56-63.
Robinson, M.A. et al., "Complexes Derived from Strong Field Ligands. XVII. Electronic Spectra of Octahedral Nickel(II) Complexes with Ligands of the α-Diimine and Closely Related Classes," Inorganic Chem., v. 2, n. 6, (1963), pp. 1178-1181.
Saito, T. et al., "1,4-Bis(trimethylsilyl)-,4-diaza-2,5-cyclohexadienes as Strong Salt-Free Reductants for Generating Low-Valent Early Transition Metals with Electron-Donating Ligands," J. Am. Chem. Soc. 2014, 136, pp. 5161-5170.
Svoboda, M. et al., "Bis(diazadien)metal(O)-Komplexe, III [1]1 Nickel(I)-bis(chelate) mit aliphatischen N-Substituenten," Z. Naturforsch. 86b, (1981), pp. 814-822—English Abstract.
Thompson, R.K. "Amidate Complexes of the Group 4 Metals," Synthesis, Reactivity, and Hydroaminiation Catalysis. Thesis, The University of British Columbia. http://hdl.handle.net/2429/1344. Available online Nov. 8, 2008, pp. 1-120.
Tsurugi, H. et al., "Carbon Radical Generation by D0 Tantalum Complexes with α-Diimine Ligands through Ligand-Centered Redox Processes," J. Am. Chem. Soc. 2011, 133, pp. 18673-18683.
Tsurugi, H. et al., "Salt-Free Reducing Reagent of Bis(trimethylsilyl)cyclohexadiene Mediates Multielectron Reduction of Chloride Complexes of W(VI) and W(IV)," J. Am. Chem. Soc. 2013, 135, pp. 5986-5989.
Vidjayacoumar et al., "Investigation of AlMe3, BEt3, and ZnEt2 as Co-Reagents for Low Temperature Copper Metal ALD/Pulsed-CVD," Chem. Mater. 2010, v. 22, pp. 4844-4853.
Yilmaz, F. et al., "Bis-(5,5'-diethylbarbiturato) Copper(II) and Cadmium(II Complexes with Ethylenediamine. Synthesis Crystal Structures, Spectroscopic and Thermal Characterization of cis-[Cu(barb)2(en] and {[Cd(barb)2(μ-en)] -2H2O)n," Z. Anorg. Allg. Chem. 2005, v. 631, pp. 1536-1540.
Non-Final Office Action mailed Apr. 7, 2014 in U.S. Appl. No. 13/319,793 filed 100/10/2011, 7 pgs.
Non-Final Office Action mailed May 28, 2014 in U.S. Appl. No. 13/493,560, filed Jun. 11, 2012, 7 pgs.
Authors et al.: Disclosed Anonymously, IP.com Prior Art Database Technical Disclosure, IP.com No. IPCOM000173198D, Jul. 25, 2008.
Non-Final Office Action mailed Aug. 27, 2014 in U.S. Appl. No. 13/818,154, filed Feb. 21, 2013, 9 pgs.
Final Office Action Mailed Sep. 24, 2014 in U.S. Appl. No. 13/493,560, filed Jun. 11, 2012, 23 pgs.
Non-final Office Action mailed Jan. 30, 2015 in U.S. Appl. No. 14/318,501, filed Jun. 27, 2014, 10 pgs.
Non-Final Office Action mailed Jan. 14, 2015 in U.S. Appl. No. 13/930,471, filed Jun. 28, 2013, 7 pgs.
Ripin, D. H. et al., "Chem 206 pKa's of Inorganic and Oxo-Acids", http://evans.harvard.edu/pdf/evans_pKa_table.pdf, Nov. 4, 2005, 6 pgs.
Non-final Office Action mailed Oct. 8, 2015 in U.S. Appl. No. 14/130,987, filed Apr. 14, 2014, 21 pgs.

* cited by examiner formic acid alkyl carboxylic acid oxalic acid dicarboxylic acids sulfonic acids

HX

Inorganic Acid $H_3PO_4$ phosphoric acid $H_3PO_2$ phosphorous acid $R^4$ = H, $C_1$-$C_8$alkyl, $C_6$-$C_{12}$aryl, $C_1$-$C_8$fluoroalkyl
X = $N_3^-$, $NO_3^-$, halide(e.g., Cl, F, Br)
n = an integer from 1 to 6.

SYNTHESIS AND CHARACTERIZATION OF FIRST ROW TRANSITION METAL COMPLEXES CONTAINING α-IMINO ALKOXIDES AS PRECURSORS FOR DEPOSITION OF METAL FILMS

FIELD OF THE INVENTION

In at least one aspect, the present invention is related to the formation of metal films from "metalorganic" precursors.

BACKGROUND OF THE INVENTION

The growth of thin films is a central step in the fabrication of many functional materials and devices. While film growth efforts have been traditionally directed toward films greater than 100 nm, recent trends in several areas are calling for the growth of films ranging in thickness from a few atomic layers up to tens of nanometers.

In the microelectronics area, copper has replaced aluminum as the interconnect material in integrated circuits due to its lower resistivity and higher resistance to electromigration. Ultrathin (2-8 nm) manganese-silicon-oxygen layers have been proposed as replacements for existing nitride-based copper diffusion barrier layers in future devices. Since copper does not nucleate well on $SiO_2$ and other surfaces, it is difficult to deposit copper metal onto the surface features of microelectronic substrates. Accordingly, there has been considerable interest in the formation of seed layers of metals such as chromium, cobalt, and others which adhere better to substrates, and upon which copper films can be subsequently grown.

Atomic layer deposition ("ALD") is a thin film deposition technique that addresses many of the current technological demands. ALD affords inherently conformal coverage and sub-nanometer film thickness control due to its self-limited growth mechanism. In a typical ALD process, a substrate is contacted with a first chemical composition that modifies the substrate for a first predetermined period of time (a pulse). Such modification involves adsorption to the surface of the substrate, reaction with the surface of the substrate, or a combination of adsorption and reaction. A purging gas is introduced to remove any lingering first gaseous chemical composition in the vicinity of the substrate. A second gaseous chemical composition that reacts with the modified substrate surface is introduced for a second predetermined period of time into the vicinity of the substrate to form a portion of the thin film. A purging gas is subsequently introduced to remove any lingering second chemical composition in the vicinity of the substrate. These steps of contacting the substrate with the first chemical composition, purging, contacting the substrate with the second gaseous chemical composition, and purging are usually repeated a plurality of times until a film of desired thickness is coated onto the substrate. Although the prior art ALD processes work well, there is unfortunately only a limited number of chemical precursors having the requisite thermal stability, reactivity, and vapor pressure for ALD.

Accordingly, there is a need for improved methods for depositing thin films by atomic layer deposition.

SUMMARY OF THE INVENTION

The present invention solves one or more problems of the prior art by providing a compound for forming a metal-containing compound or metal-containing film or powder. The compound of this embodiment is described by formula (I):

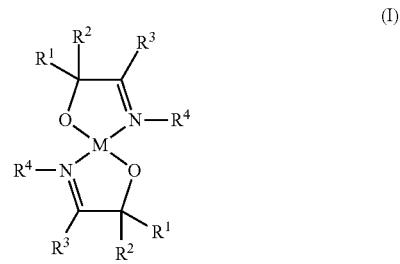

wherein

M is a metal selected from Groups 2 through 12 of the Periodic Table; and $R^1$, $R^2$, $R^3$, and $R^4$ are each independently H or $C_1$-$C_8$ alkyl.

In another embodiment, a method of forming a metal-containing product is provided. The method comprises contacting a compound having formula I as set forth above with an activating agent to form a metal-containing product.

In another embodiment, a method of forming a metal-containing film by an atomic layer deposition process is provided. The method comprises a deposition which includes contacting the substrate with vapor of a compound having formula I as set forth above such that at least a portion of the vapor of the compound having formula I adsorbs or reacts with a substrate surface to form a modified surface. The deposition cycle further includes contacting the modified surface with a vapor of an activating agent to react and form at least a portion of the metal-containing film.

In still another embodiment, a method of forming a metal-containing film on a substrate is provided. The method includes a deposition cycle that includes contacting a substrate with a vapor of a metal-containing compound described by formula I for a first predetermined pulse time to form a first modified surface:

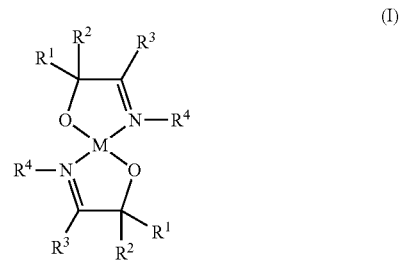

wherein:

M is a metal selected from Groups 2 to 12 of the Periodic Table; and $R^1$, $R^2$, $R^3$, and $R^4$ are each independently H or $C_1$-$C_8$ alkyl. The first modified surface is contacted with an acid for a second predetermined pulse time to form a second modified surface. The second modified surface is contacted with an activating agent for a third predetermined pulse time to form a metal layer.

BRIEF DESCRIPTION OF THE DRAWINGS

Exemplary embodiments of the present invention will become more fully understood from the detailed description and the accompanying drawings, wherein.

DESCRIPTION OF THE INVENTION

Figure 1:
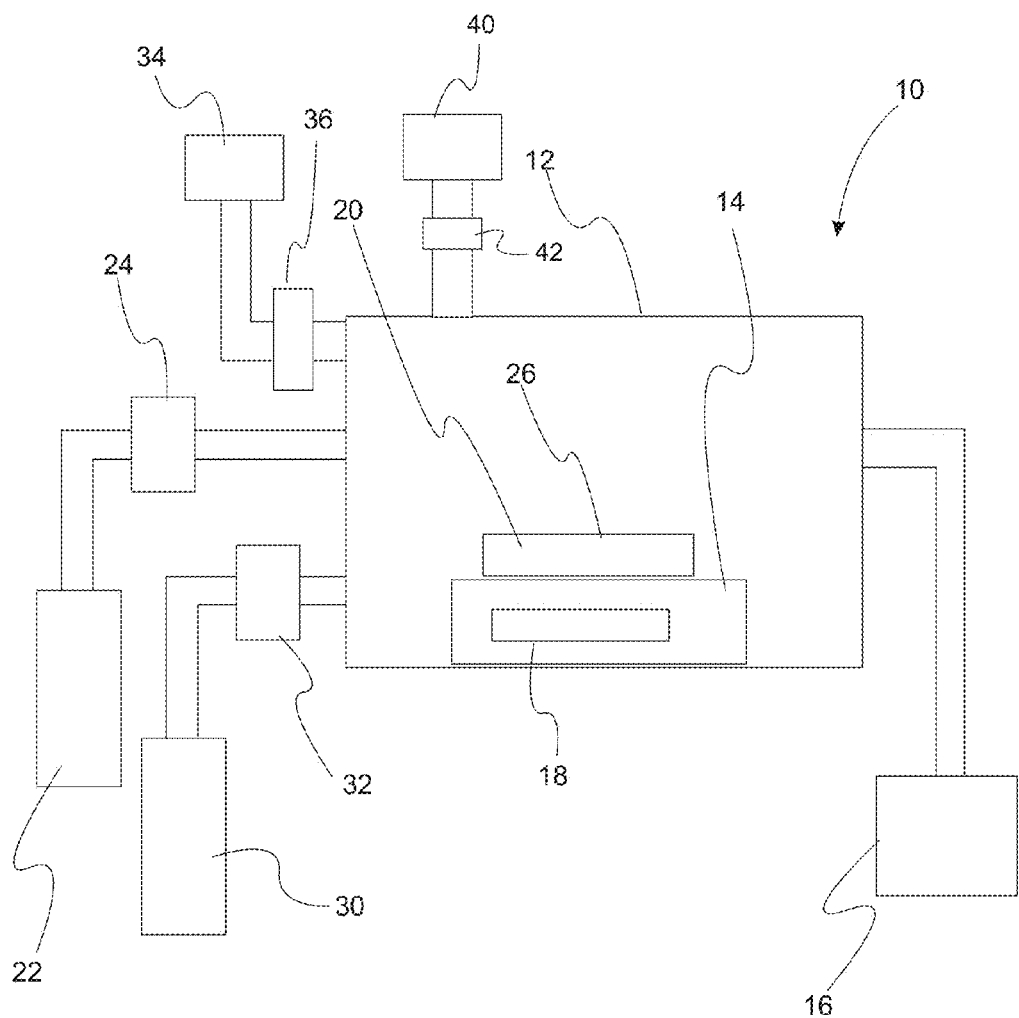
FIG. 1 is a schematic illustration of an ALD deposition system used in an embodiment of the present invention.

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment, a compound that is useful for forming a metal-containing film or product is provided. The compound of this embodiment is described by formula (I):

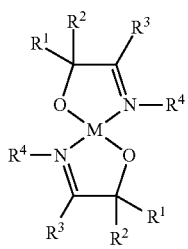
(I)

wherein

M is a metal selected from Groups 2 to 12 of the Periodic Table; and $R^1$, $R^2$, $R^3$, and $R^4$ are each independently H or $C_1$-$C_8$ alkyl. In a refinement, $R^1$, $R^2$, $R^3$, and $R^4$ are each independently methyl, ethyl, n-propyl, isopropyl, n-butyl, sec-butyl, isobutyl, or t-butyl. In another refinement, M is Cu, Cr, Mn, Fe, Co, or Ni. Specific examples of compounds having formula (I) include, but are not limited to, bis(1-(tert-butylimino)-2,3,3-trimethylbutan-2-olate)nickel(II), bis(1-(tert-butylimino)-2,3,3-trimethylbutan-2-olate)cobalt(II), bis(1-(tert-butylimino)-2,3,3-trimethylbutan-2-olate)iron(II), bis(1-(tert-butylimino)-2,3,3-trimethylbutan-2-olate)manganese(II), bis(1-(tert-butylimino)-2,3,3-trimethylbutan-2-olate)chromium(II) (5), bis(1-(tert-butylimino)-2,3,3-trimethylbutan-2-olate)copper(II), bis(1-(tert-butylimino)-2,3-dimethylbutan-2-olate)nickel(II), bis(1-(tert-butylimino)-2,3-dimethylbutan-2-olate)cobalt(II), bis(1-(tert-butylimino)-2,3-dimethylbutan-2-olate)iron(II), bis(1-(tert-butylimino)-2,3-dimethylbutan-2-olate)copper(II), bis(3-((tert-butylimino)methyl)-2,2,4,4-tetramethylpentan-3-olate)manganese(II), bis(3-((tert-butylimino)methyl)-2,2,4,4-tetramethylpentan-3-olate)copper(II), bis(3-(isopropylimino)-2-methylbutan-2-olate)nickel(II), bis(3-(isopropylimino)-2-methylbutan-2-olate)cobalt(II), bis(3-(isopropylimino)-2-methylbutan-2-olate)iron(II), bis(3-(isopropylimino)-2-methylbutan-2-olate)manganese(II), bis(3-(isopropylimino)-2-methylbutan-2-olate)chromium(II), bis(3-(isopropylimino)-2-methylbutan-2-olate)copper(II), bis(3-(2,2-dimethylhydrazono)-2-methylbutan-2-olate)nickel(II), bis(3-(2,2-dimethylhydrazono)-2-methylbutan-2-olate)cobalt(II) (20), bis(3-(2,2-dimethylhydrazono)-2-methylbutan-2-olate)iron(II), bis(3-(2,2-dimethylhydrazono)-2-methylbutan-2-olate)manganese(II), bis(3-(2,2-dimethylhydrazono)-2-methylbutan-2-olate)chrolium(II), and bis(3-(2,2-dimethylhydrazono)-2-methylbutan-2-olate)copper(II).

In another refinement of the present embodiment, a method for forming a metal or metal-containing compound is provided. In this context, the metal is characterized in having metal atoms in the zero oxidation state. The method comprises contacting a compound selected from the group of compounds having formula (I) with a compound with a reducing agent. Examples of reducing agents that can be used in this reaction include, but are not limited to, $NH_2NMe_2$, $NH_2NH_2$, $AlEt_3$, $AlMe_3$, $HSiEt_3$, $LiBHEt_3$, $LiAlH_4$, $BH_3.N(C_2H_5)_3$, $BH_3.NH(CH_3)_2$, pinacol borane, $BH_3.S(CH_3)_2$, $BH_3.THF$, $BH_3.2$-picoline, decaborane, 9-Borabicyclo[3.3.1]nonane (9-BBN), $BH_3.morpholine$, and the like. The present refinement can be carried out either in solution or in the vapor phase (e.g. ALD, chemical vapor deposition, etc.) at temperatures from about 50 to 400° C. In another refinement, the metal deposition is carried out at temperatures from about 75 to 200° C.

In a further refinement, a method of forming a metal film or metal-containing film by an atomic layer deposition process is provided. The method comprises a deposition cycle which includes contacting the substrate with vapor of a compound having formula I as set forth above such that at least a portion of the vapor of the compound having formula I adsorbs or reacts with a substrate surface to form a modified surface. The deposition cycle further includes contacting the modified surface with a vapor of a reducing agent to react and form at least a portion of the metal film. Typically, the compound having formula I is contacted with the reducing agent at a temperature from about 50 to 400° C. Examples of reducing agents that can be used in this reaction include, but are not limited to, $NH_2NMe_2$, $NH_2NH_2$, $AlEt_3$, $AlMe_3$, $HSiEt_3$, $LiBHEt_3$, $LiAlH_4$, $BH_3.N(C_2H_5)_3$, $BH_3.NH(CH_3)_2$, pinacol borane, $BH_3.S(CH_3)_2$, $BH_3.THF$, $BH_3.2$-picoline, decaborane, 9-Borabicyclo[3.3.1]nonane (9-BBN), $BH_3.morpholine$, and the like. The present reaction is used in an ALD process as set forth below. In a variation, an alloy is formed by alternating ALD deposition cycles using a compound having formula I and a reducing agent with cycles using another metal containing compound. For example, deposition of a metal film might involve 1-50 cycles of compound I and a reducing agent followed by 1-50 cycles of another metal containing compound and a reducing agent. These cycles are repeated to provide an alloy of a predetermined thickness.

With reference to FIG. 1, deposition system 10 includes reaction chamber 12, substrate holder 14, and vacuum pump 16. Typically, the substrate is heated via heater 18. The method has a deposition cycle comprising contacting substrate 20 with a vapor of a metal-containing compound described by formula I as set forth above. In particular, the vapor is introduced from precursor source 22 into reaction chamber 12 for a first predetermined pulse time (e.g., 1 second to 20 seconds). The first pulse time is controlled via control valve 24. At least a portion of the vapor of the metal-containing compound modifies (e.g, adsorbs or reacts with) substrate surface 26 to form a modified surface. The method further comprises contacting the modified surface with a vapor of an activating agent as set forth above from source 30 for a second predetermined pulse time (e.g., 1 second to 20 seconds). The second predetermined pulse time is controlled via control valve 32. In a refinement, the activating agent is a reducing agent which causes the metal-containing compound to react and form at least a portion of the thin metal film on the surface of the substrate. The reduced pressure of chamber 12 is maintained by vacuum pump 16. In another refinement, the activating agent is an oxidizing agent which results in a metal oxide layer being formed. Examples of useful oxidizing agents include, but are not limited to, water, ozone, molecular oxygen, atomic oxygen, organic alcohols, hydrogen peroxide, organic hydroperoxides, organic peroxides, nitrous oxide, plasma-activated versions of the above compounds. In still another refinement, the activating agent is a nitriding agent (i.e., a nitrogen-containing compound) which results in a metal nitride layer. Examples of such nitrogen activating compounds include, but are not limited to, ammonia, hydrazine, alkyl-substituted hydrazines, and plasma activated versions thereof.

In a variation of the present embodiment, the method further comprises removing at least a portion of the vapor of the metal containing compound having formula I that is lingering in the gas phase (i.e., has not adsorbed or reacted with the substrate) from the vicinity of the substrate before introducing the vapor of the reducing agent and removing at least a portion of the vapor of the reducing agent from the vicinity of the substrate. The metal-containing compound and the reducing agent are removed in purging steps by introducing a purge gas from purge source 34 into reaction chamber 12 for a predetermined purge time (e.g., 0.5 seconds to 2 minutes). The purge time is controlled by control valve 36.

In another variation, the method further includes at least one additional deposition cycle comprising sequentially contacting the substrate with the vapor of a metal-containing compound having formula I and then the vapor of the reducing agent. In some refinements, the substrate is contacted for a plurality of additional deposition cycles. For example, the substrate may be contacted with from 1 to several thousand deposition cycles depending on the thickness of the film desired. In particular, the substrate is contacted with the vapor of a metal-containing compound having formula I and then the vapor of the reducing agent for 1 to 5000 deposition cycles. In another refinement, the substrate is contacted with the vapor of a metal-containing compound having formula I and then the vapor of the reducing agent for 10 to 2000 deposition cycles. In still another refinement, the substrate is contacted with the vapor of a metal-containing compound having formula I and then the vapor of the reducing agent for 20 to 1000 deposition cycles.

In a variation of the present embodiment, a nucleation cycle precedes deposition of the metal-containing film as set forth above. In such a nucleation cycle, substrate 20 is contacted with a vapor of a metal-containing compound described by formula I as set forth above. In particular, the vapor is introduced from precursor source 22 into reaction chamber 12 for a predetermined nucleation pulse time. The pulse time is controlled via control valve 24. At least a portion of the vapor of the metal-containing compound modifies (e.g, adsorbs or reacts with) substrate surface 26 to form a modified surface. The method further comprises contacting the modified surface with a vapor of an activating agent as set forth above from source 30 for a predetermined pulse time. Typically, the nucleation pulse time is greater than the first pulse predetermined pulse time. Films grown without nucleation cycle tend to have very low growth rates. Nucleation step helps to increase the nucleation and thereby increases the growth rate. In nucleation cycle, long pulses (e.g about 20 seconds(s)) of metal precursor are applied so that the precursor can react or chemisorb to the surface enhancing nucleation. In a refinement, 10 to 200 nucleation cycles are employed prior to the ALD run. In another nucleation strategy, formic acid is used to enhance the nucleation. In particular, formic acid is incorporated to the previously described nucleation cycle. In an example of this latter method, Ni films are deposited on Ru, silicon with native oxide, thermal $SiO_2$, Pt, Pd, and TiN substrates. Without such nucleation, Ni films were not deposited on substrates other than Ru. An example of such a nucleation is 100 cycles of a HCOOH pulse time of 0.3 seconds (s), HCOOH purge time of 5.0 s, Ni(iPrMeCOCNtBu)$_2$ pulse time of 20.0 s, Ni(iPrMeCOCNtBu)$_2$ purge time of 5.0 s, $BH_3.NHMe_2$ pulse time of 1.0 s, and $BH_3.NHMe_2$ purge time 10.0 s. This is followed by 1000 cycles of Ni(iPrMeCOCNtBu)$_2$ with a pulse time of 3.0 s, Ni(iPrMeCOCNtBu)$_2$ with a purge time of 5.0 s, $BH_3.NHMe_2$ pulse time of 1.0 s, and $BH_3.NHMe_2$ purge time of 10.0 s In another embodiment, a method of forming a metal-containing film is provided. With reference to FIG. 1, the vapor of a compound having formula I is introduced from precursor source 22 into reaction chamber 12 for a first predetermined pulse time. The first predetermined pulse time should be sufficiently long that available binding sites on the substrate surface (coated with metal layers or uncoated) are saturated (i.e., metal-containing compound attached). Typically, the first predetermined pulse time is from 1 second to 20 seconds. The first predetermined pulse time is controlled via control valve 24. At least a portion of the vapor of the metal-containing compound modifies (e.g, adsorbs or reacts with) substrate surface 26 to form a first modified surface. Reaction chamber 12 is then purged with an inert gas for a first purge time. The first purge time is sufficient to remove the metal-containing compound from reaction chamber 12 and is typically from 0.5 seconds to 2 minutes.

Figure 2:
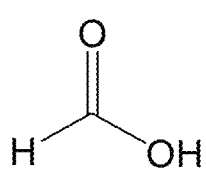
FIG. 2 provides examples of acids that can be reacted with the compounds of formula I.
Figure 2:
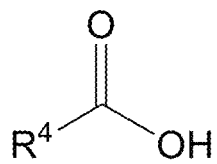
Figure 2:
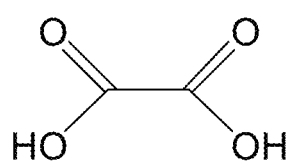
Figure 2:
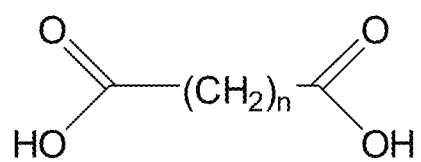
Figure 2:
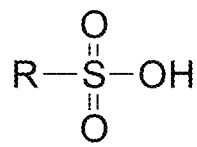

In the next reaction step of the deposition cycle, an acid such as formic acid is then introduced from acid source 40 into reaction chamber 12 for a second predetermined pulse time. Examples of other suitable acids are provided in FIG. 2. In FIG. 2, $R^4$ is H (i.e., hydride), $C_{1-8}$ alkyl, $C_{6-12}$ aryl, or $C_{1-8}$ fluoroalkyl, X is $N_3^-$, $NO_3^-$, halide (e.g., Cl, F, Br), and n is an integer from 1 to 6. In a refinement, $R^4$ is hydride, $C_{1-4}$ alkyl, $C_{6-10}$ aryl, or $C_{1-4}$ fluoroalkyl, X is $N_3^-$, $NO_3^-$, halide (e.g., Cl, F, Br), and n is an integer from 1 to 6. Examples of useful alkyl groups include, but are not limited to, methyl, ethyl, n-propyl, isopropyl, n-butyl, t-butyl, isobutyl, sec-butyl, and the like. Examples of useful aryl groups include, but are not limited to, phenyl, tolyl, naphthyl, and the like. The second predetermined pulse time should be sufficiently long that available binding sites on the first modified substrate surface are saturated and a second modified surface is formed. Typically, the second predetermined pulse time is from 0.1 second to 20 seconds. The second predetermined pulse time is controlled via control valve 32. Reaction chamber 12 is then purged with an inert gas for a second purge time (typically, 0.5 seconds to 2 minutes as set forth above).

In the final reaction step of the deposition cycle, a reducing agent is then introduced from activating agent source 30 into reaction chamber 12 for a third predetermined time. In a refinement, the activating agent is an oxidizing agent, reducing agent or nitriding agent as set forth above. The third predetermined pulse time should be sufficiently long that available binding sites on the second modified substrate surface are saturated with a metal layer being formed thereon. Typically, the third predetermined pulse time is from 0.1 second to 20 seconds. Reaction chamber 12 is then purged with an inert gas for a third purge time (typically, 0.5 seconds to 2 minutes as set forth above).

During film formation by the methods set forth above, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

Experimental Section

General Considerations.

All manipulations were carried out under argon using either Schlenk or glove box techniques. (Preparation of ligands was done under ambient conditions). Tetrahydrofuran was distilled from sodium benzophenone ketyl, hexane was distilled from $P_2O_5$. Anhydrous transition-metal chlorides ($CrCl_2$, $MnCl_2$, $FeCl_2$, $CoCl_2$, and $NiCl_2$) were obtained from Strem Chemicals Inc. and used as received. $NiCl_2 \cdot CH_3CN$ was prepared according to a literature procedure Reedijk, J.; Groeneveid, W. L., RECL. TRAV. CHIM. PAYS-BAS 1968, 87, 552. Potassium hydride (30 wt % dispersion in mineral oil; washed with hexane before use), tert-butyl amine, methyl lithium and 1,1-dimethylhydrazine were purchased from Sigma-Aldrich. tert-butyl hydrazine hydrochloride was purchased from Across Organics. Glyoxal and 3-hydroxy-3-methyl-2-butanone were purchased from Alfa Aesar.

$^1H$ and $^{13}C\{^1H\}$ NMR spectra were obtained at 400 and 100 MHz in benzene-$d_6$ or chloroform-$d_1$ and were referenced to the residual proton and the $^{13}C$ resonances of the solvents. IR spectra were obtained using Nujol as the medium. Melting points were obtained on a Thermo Scientific Mel-Temp 3.0 digital melting point apparatus and are uncorrected. Thermogravimetric analyses (TGA) were carried out with a SDT-2960 TGA/DTA instrument.

Reaction schemes S1 and S2 provide methods for the preparation of ligands;

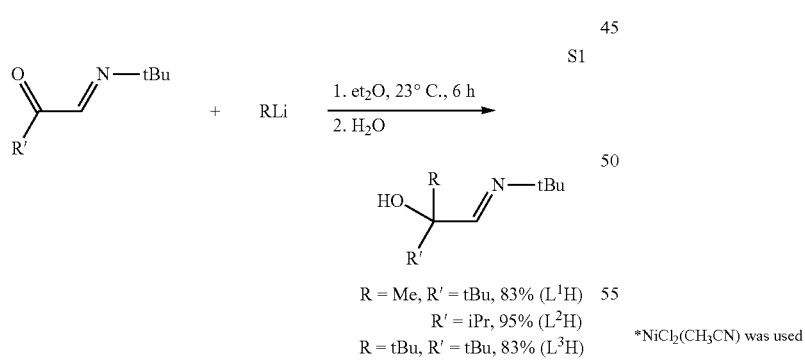

Reaction schemes S3 and S4 provide methods for the preparation of the complexes:

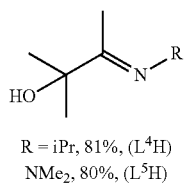

R = iPr, 81%, ($L^4H$)
$NMe_2$, 80%, ($L^5H$)

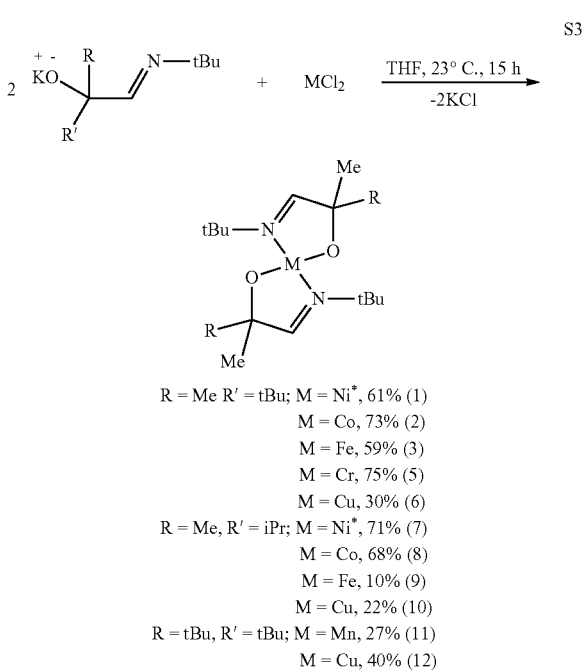

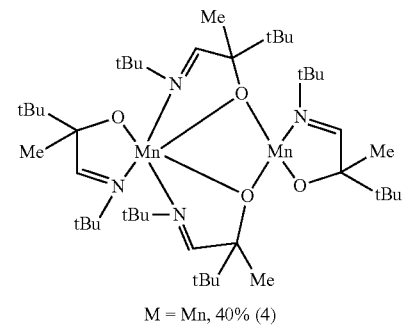

M = Mn, 40% (4)

*$NiCl_2(CH_3CN)$ was used

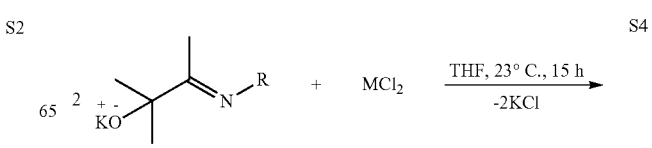

-continued

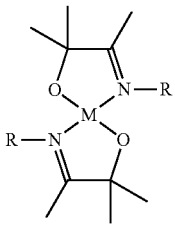

R = iPr; M = Ni, 74% (13)
M = Co, 61% (14)
M = Cr, 68% (17)
M = Cu, 71% (18)
R = NMe₂; M = Ni, 77% (19)
M = Co, 60% (20)
M = Cr, 49% (23)
M = Cu, 75% (24)

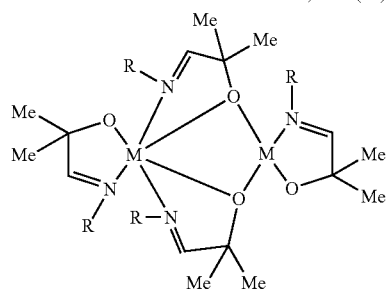

R = iPr, M = Fe, 68% (15)
Mn, 68% (16)
R = NMe₂, M = Fe, 63% (21)
Mn, 53% (22)

Preparation of 1-(tert-butylimino)-2,3,3-trimethylbutan-2-ol (L$^1$H)

A 100 mL round bottom flask was charged with a magnetic stir bar, 1-(tert-butylimino)-3,3-dimethylbutan-2-one (1.000 g, 5.91 mmol) and diethyl ether (20 mL). To this stirred solution at ambient temperature was slowly added 1.6 M methyl lithium (4.1 mL, 6.50 mmol), and solution was stirred for 12 h. The resultant yellow solution was washed with water and organic layer was separated. Organic layer was dried over Na$_2$SO$_4$ and diethyl ether was removed under reduced pressure. Light yellow oil was obtained by vacuum distillation of the crude oil at 60° C./0.05 Torr (0.908 g, 83%): $^1$H NMR (CDCl$_3$, 23° C., δ) 7.68 (s, 1H, CHN), (s, broad, 1H, OH), 1.17 (s, 9H, C(CH$_3$)$_3$), 1.16 (s, 3H, CH$_3$), 0.90 (s, 9H, C(CH$_3$)$_3$); $^{13}$C {$^1$H} NMR, (chloroform-d$_1$, 23° C., ppm) 160.59 (s, CHN), 75.37 (s, C(OH)), 56.21 (s, C(CH$_3$)$_3$), 37.32 (s, C(CH$_3$)$_3$), 29.64 (s, C(CH$_3$)$_3$), 25.36 (s, C(CH$_3$)$_3$), 20.85 (s, CCH$_3$); ESI-HRMS: calcd for C$_{11}$H$_{24}$NO ([M+H]$^+$) 186.1857. found 186.1858.

Preparation of 1-(tert-butylimino)-2,3-dimethylbutan-2-ol (L$^2$H)

In a fashion similar to the preparation of L$^1$H, treatment of 1-(tert-butylimino)-3-methylbutan-2-one (1.000 g, 6.44 mmol) in diethyl ether (20 mL) with 1.6 M methyl lithium (4.4 mL, 7.08 mmol) for 12 h at ambient temperature afforded L$^2$H (1.048 g, 95%) light yellow liquid upon vacuum distillation at 55° C./0.05 Torr: $^1$H NMR (benzene-d$_6$, 23° C., δ) 7.34 (s, 1H, CHN), 4.59 (s, broad, 1H, OH), 1.62 (sep, 1H, CH(CH$_3$)$_2$), 1.15 (s, 3H, CH$_3$), 1.03 (s, 9H, C(CH$_3$)$_3$), 1.00 (d, (J=6.8), 3H, CHCH$_3$), 0.82 (d, (J=7.2), 3H, CHCH$_3$); $^{13}$C {$^1$H} NMR, (benzene-d$_6$, 23° C., ppm) 162.10 (s, CHN), 73.86 (s, C(OH)), 56.01 (s, C(CH$_3$)$_3$), 36.14 (s, CH(CH$_3$)$_2$), 29.65 (s, C(CH$_3$)$_3$), 23.95 (s, CH (CH$_3$)$_2$), 17.55 (s, CH(CH$_3$)$_2$); ESI-HRMS: calcd for C$_{10}$H$_{22}$NO ([M+H]$^1$) 172.1701. found 172.1701.

Preparation of 3-((tert-butylimino)methyl)-2,2,4,4-tetramethylpentan-3-ol (L$^3$H)

In a fashion similar to the preparation of L$^1$H, treatment of 1-(tert-butylimino)-3,3-dimethylbutan-2-one (1.000 g, 5.91 mmol) in diethyl ether (20 mL) with 1.7 M tert-butyl lithium (3.8 mL, 6.50 mmol) for 12 h at ambient temperature afforded L$^3$H (1.113 g, 83%) light yellow liquid upon vacuum distillation at 65° C./0.05 Torr: $^1$H NMR (benzene-d$_6$, 23° C., δ) 7.78 (s, 1H, CHN), 4.99 (s, 1H, OH), 1.11 (s, 18H, C(CH$_3$)$_3$), 1.03 (s, 9H, C(CH$_3$)$_3$); $^{13}$C {$^1$H} NMR, (benzene-d$_6$, 23° C., ppm) 161.07 (s, CHN), 95.03 (s, C(OH)), 40.29 (s, C(CH$_3$)$_3$), 29.49 (s, C(CH$_3$)$_3$), 28.89 (s, C(CH$_3$)$_3$).

Preparation of 3-(isopropylimino)-2-methylbutan-2-ol (L$^4$H)

A 100-mL round bottom flask, equipped with a magnetic stir bar, molecular sieves (4 Å, 4.0 g), and a reflux condenser, was charged with 3-hydroxy-3-methyl-2-butanone (2.000 g, 19.58 mmol), isopropylamine (11.575 g, 195.8 mmol), and benzene (25 mL). The solution was refluxed for 18 h, filtered through a 1-cm pad of Celite on a coarse glass frit, and the volatiles were then removed under reduced pressure, yielding pale yellow oil. The oil was distilled at 60° C./0.05 Torr to afford L$^1$H as a colorless liquid (2.270 g, 81%): IR (neat liquid, cm$^{-1}$) 3321 (v$_{OH}$, br), 1667 (v$_{C=N}$, s); $^1$H NMR (C$_6$D$_6$, 23° C., δ) 6.03 (br s, 1H, OH), 3.32 (sept, 1H, CH(CH$_3$)$_2$), 1.31 (s, 3H, CH$_3$C), 1.24 (s, 6H, CH (CH$_3$)$_2$), 0.97 (d, 6H, (CH$_3$)$_2$C).

Preparation of 3-(2,2-dimethylhydrazono)-2-methylbutan-2-ol (L$^5$H)

A 100-mL round bottom flask, equipped with a magnetic stir bar and molecular sieves (4 Å, 4.0 g), was charged with 3-hydroxy-3-methyl-2-butanone (2.000 g, 19.58 mmol), N,N-dimethylhydrazine (11.767 g, 195.8 mmol), and benzene (25 mL). The solution was stirred for 18 h at ambient temperature, filtered through a 1-cm pad of Celite on a coarse glass frit, and the volatiles were then removed under reduced pressure, yielding colorless oil. The oil was distilled at 60° C./0.05 Torr to afford L$^2$H as a colorless liquid (2.259 g, 80%): IR (neat liquid, cm$^{-1}$) 3404 (v$_{OH}$, br), 1637 (v$_{C=N}$, s); $^1$H NMR (C$_6$D$_6$, 23° C., δ) 5.13 (s, 1H, OH), 2.25 (s, 6H, N(CH$_3$)$_2$), 1.66 (s, 3H, CH$_3$C), 1.24 (s, 6H, (CH$_3$)$_2$C).

Preparation of Bis(1-(tert-butylimino)-2,3,3-trimethylbutan-2-olate)nickel(II) (1)

A 100 mL Schlenk flask was charged with a magnetic stir bar, 1-(tert-butylimino)-2,3,3-trimethylbutan-2-ol (1.000 g, 5.40 mmol) and tetrahydrofuran (30 mL). To this stirred solution at ambient temperature was slowly added potassium hydride (0.238 g, 5.94 mmol), and solution was stirred for 4 h. This solution was then slowly added dropwise by cannula to a stirred suspension of anhydrous NiCl$_2$.CH$_3$CN (0.456 g, 2.70 mmol) in tetrahydrofuran (40 mL) at −78° C. The resultant dark orange brown solution was stirred for 15 h at ambient temperature. The volatile components were then removed under reduced pressure, and the resultant brown powder was dissolved in hexane (60 mL). The solution was filtered through a 1 cm pad of celite on a coarse glass frit, and hexane was then removed under reduced pressure. Pale red crystals of 1 were obtained by sublimation at 120° C./0.05 Torr (0.702 g, 61%): mp 175-177° C.; $^1$H NMR ($C_6D_6$, 23° C., δ) 10.23 (s, 1H, CHN), 10.03 (s, 1H, CHN), 1.47 (s, 9H, $C(CH_3)_3$), 1.45 (s, 9H, $C(CH_3)_3$), 1.15 (s, 3H, $CH_3$), 1.10 (s, 9H, $C(CH_3)_3$), 1.05 (s, 9H, $C(CH_3)_3$); $^{13}C\{^1H\}$ NMR, (chloroform-d$_1$, 23° C., ppm) 164.94 (s, CHN), 163.11 (s, CHN), 65.55 (s, C(OH)), 65.11 (s, C(OH)), 33.94 (s, $CCH_3$), 33.56 (s, $CCH_3$), 26.62 (s, $C(CH_3)_3$), 26.54 (s, $C(CH_3)_3$); Anal. Calcd for $C_{22}H_{44}NiN_2O_2$: C, 61.84; H, 10.38; N, 6.56. Found: C, 61.92; H, 10.28; N, 6.44.

Preparation of Bis(1-(tert-butylimino)-2,3,3-trimethylbutan-2-olate)cobalt(II) (2)

In a fashion similar to the preparation of 1, treatment of anhydrous cobalt(II) chloride (0.350 g, 2.70 mmol) in tetrahydrofuran (40 mL) with a solution of potassium 1-(tert-butylimino)-2,3,3-trimethylbutan-2-olate (prepared from 1-(tert-butylimino)-2,3,3-trimethylbutan-2-ol (1.000 g, 5.40 mmol) and potassium hydride (0.238 g, 5.94 mmol) in tetrahydrofuran (30 mL)) for 15 h at ambient temperature afforded 2 (0.800 g, 73%) as orange crystals upon sublimation at 115° C./0.05 Torr: mp 84-86° C.; $\mu_{eff}$=1.85 and 4.06 $\mu_B$ in the solid state and in benzene solution, respectively.

Preparation of Bis(1-(tert-butylimino)-2,3,3-trimethylbutan-2-olate)iron(II) (3)

In a fashion similar to the preparation of 1, treatment of anhydrous iron(II) chloride (0.342 g, 2.70 mmol) in tetrahydrofuran (40 mL) with a solution of potassium 1-(tert-butylimino)-2,3,3-trimethylbutan-2-olate (prepared from 1-(tert-butylimino)-2,3,3-trimethylbutan-2-ol (1.000 g, 5.40 mmol) and potassium hydride (0.238 g, 5.94 mmol) in tetrahydrofuran (30 mL)) for 15 h at ambient temperature afforded 3 (0.676 g, 59%) as purple crystals upon sublimation at 85° C./0.05 Torr: mp 112-114° C.; $\mu_{eff}$=5.46 and 5.24 $\mu_B$ in the solid state and in benzene solution, respectively. Anal. Calcd for $C_{22}H_{44}FeN_2O_2$: C, 62.25; H, 10.45; N, 6.60. Found: C, 62.02; H, 10.37; N, 6.56.

Preparation of Bis(1-(tert-butylimino)-2,3,3-trimethylbutan-2-olate)manganese(II) (4)

In a fashion similar to the preparation of 1, treatment of anhydrous manganese(II) chloride (0.340 g, 2.70 mmol) in tetrahydrofuran (40 mL) with a solution of potassium 1-(tert-butylimino)-2,3,3-trimethylbutan-2-olate (prepared from 1-(tert-butylimino)-2,3,3-trimethylbutan-2-ol (1.000 g, 5.40 mmol) and potassium hydride (0.238 g, 5.94 mmol) in tetrahydrofuran (30 mL)) for 15 h at ambient temperature afforded 4 (0.457 g, 40%) as off white crystals upon sublimation at 160° C./0.05 Torr: mp 220-223° C.; $\mu_{eff}$=8.08 and 8.04 $\mu_B$ in the solid state and in benzene solution, respectively. Anal. Calcd for $C_{22}H_{44}MnN_2O_2$: C, 62.39; H, 10.47; N, 6.61. Found: C, 62.22; H, 10.32; N, 6.40.

Preparation of Bis(1-(tert-butylimino)-2,3,3-trimethylbutan-2-olate)chromium(II) (5)

In a fashion similar to the preparation of 1, treatment of anhydrous chromium(II) chloride (0.332 g, 2.70 mmol) in tetrahydrofuran (40 mL) with a solution of potassium 1-(tert-butylimino)-2,3,3-trimethylbutan-2-olate (prepared from 1-(tert-butylimino)-2,3,3-trimethylbutan-2-ol (1.000 g, 5.40 mmol) and potassium hydride (0.238 g, 5.94 mmol) in tetrahydrofuran (30 mL)) for 15 h at ambient temperature afforded 5 (0.852 g, 75%) as pale green crystals upon sublimation at 115° C./0.05 Torr: mp 173-175° C.; $\mu_{eff}$=4.75 and 4.91 $\mu_B$ in the solid state and in benzene solution, respectively. Anal. Calcd for $C_{22}H_{44}CrN_2O_2$: C, 62.82; H, 10.54; N, 6.66. Found: C, 62.96; H, 10.35; N, 6.43.

Preparation of Bis(1-(tert-butylimino)-2,3,3-trimethylbutan-2-olate)copper(II) (6)

In a fashion similar to the preparation of 1, treatment of anhydrous copper(II) chloride (0.363 g, 2.70 mmol) in tetrahydrofuran (40 mL) with a solution of potassium 1-(tert-butylimino)-2,3,3-trimethylbutan-2-olate (prepared from 1-(tert-butylimino)-2,3,3-trimethylbutan-2-ol (1.000 g, 5.40 mmol) and potassium hydride (0.238 g, 5.94 mmol) in tetrahydrofuran (30 mL)) for 15 h at ambient temperature afforded 6 (0.350 g, 30%) as purple crystals upon sublimation at 130° C./0.05 Torr: mp 163-165° C.; $\mu_{eff}$=1.79 and 1.75 $\mu_B$ in the solid state and in benzene solution, respectively. Anal. Calcd for $C_{22}H_{44}CuN_2O_2$: C, 61.15; H, 10.26; N, 6.48. Found: C, 61.05; H, 9.98; N, 6.51.

Preparation of Bis(1-(tert-butylimino)-2,3-dimethylbutan-2-olate)nickel(II) (7)

In a fashion similar to the preparation of 1, treatment of anhydrous $NiCl_2.CH_3CN$ (0.490 g, 2.92 mmol) in tetrahydrofuran (40 mL) with a solution of potassium 1-(tert-butylimino)-2,3-dimethylbutan-2-olate (prepared from 1-(tert-butylimino)-2,3-dimethylbutan-2-ol (1.000 g, 5.84 mmol) and potassium hydride (0.257 g, 6.42 mmol) in tetrahydrofuran (30 mL)) for 15 h at ambient temperature afforded 7 (0.810 g, 71%) as pale red crystals upon sublimation at 90° C./0.05 Torr: mp 125-127° C.; $^1$H NMR ($C_6D_6$, 23° C., δ) 10.91 (s, 1H, CHN), 10.60 (s, 1H, CHN), 1.74 (sep, 1H, $CH(CH_3)_2$), 1.58 (s, 9H, $C(CH_3)_3$), 1.55 (s, 9H, $C(CH_3)_3$), 1.31 (s, 3H, $CH_3$), 1.22 (s, 3H, $CH_3$), 1.031 (d, 6H, $C(CH_3)_2$), 0.952 (d, 6H, $C(CH_3)_2$).

Preparation of Bis(1-(tert-butylimino)-2,3-dimethylbutan-2-olate)cobalt(II) (8)

In a fashion similar to the preparation of 1, treatment of anhydrous cobalt (0.376 g, 2.92 mmol) in tetrahydrofuran (40 mL) with a solution of potassium 1-(tert-butylimino)-2,3-dimethylbutan-2-olate (prepared from 1-(tert-butylimino)-2,3-dimethylbutan-2-ol (1.000 g, 5.84 mmol) and potassium hydride (0.257 g, 6.42 mmol) in tetrahydrofuran (30 mL)) for 15 h at ambient temperature afforded 8 (0.791 g, 68%) as green crystals upon sublimation at 90° C./0.05 Torr: mp 96-98° C.; $\mu_{eff}$=3.78 and 3.94 $\mu_B$ in the solid state and in benzene solution, respectively.

Preparation of Bis(1-(tert-butylimino)-2,3-dimethylbutan-2-olate)iron(II) (9)

In a fashion similar to the preparation of 1, treatment of anhydrous iron (0.367 g, 2.92 mmol) in tetrahydrofuran (40 mL) with a solution of potassium 1-(tert-butylimino)-2,3-dimethylbutan-2-olate (prepared from 1-(tert-butylimino)-2,3-dimethylbutan-2-ol (1.000 g, 5.84 mmol) and potassium hydride (0.257 g, 6.42 mmol) in tetrahydrofuran (30 mL))

for 15 h at ambient temperature afforded 9 (0.116 g, 10%) as purple crystals upon sublimation at 75° C./0.05 Torr: mp 92-94° C.

Preparation of Bis(1-(tert-butylimino)-2,3-dimethylbutan-2-olate)copper(II) (10)

In a fashion similar to the preparation of 1, treatment of anhydrous copper (0.390 g, 2.92 mmol) in tetrahydrofuran (40 mL) with a solution of potassium 1-(tert-butylimino)-2,3-dimethylbutan-2-olate (prepared from 1-(tert-butylimino)-2,3-dimethylbutan-2-ol (1.000 g, 5.84 mmol) and potassium hydride (0.257 g, 6.42 mmol) in tetrahydrofuran (30 mL)) for 15 h at ambient temperature afforded 10 (0.791 g, 22%) as purple crystals upon sublimation at 105° C./0.05 Torr: mp 134-136° C.; $\mu_{eff}$=1.70 and 1.78 $\mu_B$ in the solid state and in benzene solution, respectively. Anal. Calcd for $C_{20}H_{40}CuN_2O_2$: C, 59.45; H, 9.98; N, 693. Found: C, 59.50; H, 9.81; N, 6.87.

Preparation of Bis(3-((tert-butylimino)methyl)-2,2,4,4-tetramethylpentan-3-olate)manganese(II) (11)

In a fashion similar to the preparation of 1, treatment of anhydrous manganese(II) chloride (0.276 g, 2.20 mmol) in tetrahydrofuran (40 mL) with a solution of potassium 3-((tert-butylimino)methyl)-2,2,4,4-tetramethylpentan-3-olate (prepared from 3-((tert-butylimino)methyl)-2,2,4,4-tetramethylpentan-3-ol (1.000 g, 4.40 mmol) and potassium hydride (0.194 g, 4.84 mmol) in tetrahydrofuran (30 mL)) for 15 h at ambient temperature afforded 11 (0.150 g, 27%) as off white crystals upon sublimation at 130° C./0.05 Torr.

Preparation of Bis(3-((tert-butylimino)methyl)-2,2,4,4-tetramethylpentan-3-olate)copper(II) (12)

In a fashion similar to the preparation of 1, treatment of anhydrous copper(II) chloride (0.296 g, 2.20 mmol) in tetrahydrofuran (40 mL) with a solution of potassium 3-((tert-butylimino)methyl)-2,2,4,4-tetramethylpentan-3-olate (prepared from 3-((tert-butylimino)methyl)-2,2,4,4-tetramethylpentan-3-ol (1.000 g, 4.40 mmol) and potassium hydride (0.194 g, 4.84 mmol) in tetrahydrofuran (30 mL)) for 15 h at ambient temperature afforded 12 (0.454 g, 40%) as purple crystals upon sublimation at 135° C./0.05 Torr: mp 183-185; $\mu_{eff}$=1.82 and 1.74 $\mu_B$ in the solid state and in benzene solution, respectively.

Preparation of Bis(3-(isopropylimino)-2-methylbutan-2-olate)nickel(II) (13)

In a fashion similar to the preparation of 1, treatment of anhydrous $NiCl_2 \cdot CH_3CN$ (0.596 g, 3.49 mmol) in tetrahydrofuran (40 mL) with a solution of potassium 3-(isopropylimino)-2-methylbutan-2-olate (prepared from 3-(isopropylimino)-2-methylbutan-2-ol (1.000 g, 6.98 mmol) and potassium hydride (0.308 g, 7.68 mmol) in tetrahydrofuran (30 mL)) for 15 h at ambient temperature afforded 13 (0.885 g, 74%) as pale green crystals upon sublimation at 100° C./0.05 Torr: mp 158-160° C.; IR (Nujol, cm$^{-1}$) 1619 ($v_{C=N}$, s); $^1$H NMR ($C_6D_6$, 23° C., δ) 3.71 (br, 1H, $CH(CH_3)_2$), 1.44 (s, 3H, $CH_3C$), 1.18 (s, 6H, $CH(CH_3)_2$), 1.05 (s, 6H, $(CH_3)_2C$).

Preparation of Bis(3-(isopropylimino)-2-methylbutan-2-olate)cobalt(II) (14)

In a fashion similar to the preparation of 1, treatment of anhydrous cobalt(II) chloride (0.453 g, 3.49 mmol) in tetrahydrofuran (40 mL) with a solution of potassium 3-(isopropylimino)-2-methylbutan-2-olate (prepared from 3-(isopropylimino)-2-methylbutan-2-ol (1.000 g, 6.98 mmol) and potassium hydride (0.308 g, 7.68 mmol) in tetrahydrofuran (30 mL)) for 15 h at ambient temperature afforded 14 (0.724 g, 61%) as dark green crystals upon sublimation at 100° C./0.05 Torr: mp 158-160° C.; IR (Nujol, cm$^{-1}$) 1633 ($v_{C=N}$, s); $\mu_{eff}$=5.03 and 4.03 BM in solid state and benzene solution, respectively.

Preparation of Bis(3-(isopropylimino)-2-methylbutan-2-olate)iron(II) (15)

In a fashion similar to the preparation of 1, treatment of anhydrous iron(II) chloride (0.442 g, 3.49 mmol) in tetrahydrofuran (40 mL) with a solution of potassium 3-(isopropylimino)-2-methylbutan-2-olate (prepared from 3-(isopropylimino)-2-methylbutan-2-ol (1.000 g, 6.98 mmol) and potassium hydride (0.308 g, 7.68 mmol) in tetrahydrofuran (30 mL)) for 15 h at ambient temperature afforded 15 (0.806 g, 68%) as green crystals by crystallization at −23° C. in hexanes: mp 172-175° C.; IR (Nujol, cm$^{-1}$) 1633 ($v_{C=N}$, s); $\mu_{eff}$=8.29 and [8.58(dimer), 6.07(monomer)] BM in solid state and benzene solution, respectively.

Preparation of Bis(3-(isopropylimino)-2-methylbutan-2-olate)manganese(II) (16)

In a fashion similar to the preparation of 1, treatment of anhydrous manganese(II) chloride (0.439 g, 3.49 mmol) in tetrahydrofuran (40 mL) with a solution of potassium 3-(isopropylimino)-2-methylbutan-2-olate (prepared from 3-(isopropylimino)-2-methylbutan-2-ol (1.000 g, 6.98 mmol) and potassium hydride (0.308 g, 7.68 mmol) in tetrahydrofuran (30 mL)) for 15 h at ambient temperature afforded 16 (0.639 g, 54%) as pale yellow crystals by crystallization at −23° C. in hexanes: mp 202-203° C.; IR (Nujol, cm$^{-1}$) 1634 ($v_{C=N}$, s); $\mu_{eff}$=[8.54(dimer), 6.04(monomer)] and [8.26(dimer), 5.84 (monomer)] BM in solid state and benzene solution, respectively.

Preparation of Bis(3-(isopropylimino)-2-methylbutan-2-olate)chromium(II) (17)

In a fashion similar to the preparation of 1, treatment of anhydrous chromium(II) chloride (0.429 g, 3.491 mmol) in tetrahydrofuran (40 mL) with a solution of potassium 3-(isopropylimino)-2-methylbutan-2-olate (prepared from 3-(isopropylimino)-2-methylbutan-2-ol (1.000 g, 6.98 mmol) and potassium hydride (0.308 g, 7.68 mmol) in tetrahydrofuran (30 mL)) for 15 h at ambient temperature afforded 17 (0.797 g, 68%) as intense maroon crystals upon sublimation at 90° C./0.05 Torr: mp 143-146° C.; IR (Nujol, cm$^{-1}$) 1620 ($v_{C=N}$, s); $\mu_{eff}$=4.76 and 4.59 BM in solid state and benzene solution, respectively.

Preparation of Bis(3-(isopropylimino)-2-methylbutan-2-olate)copper(II) (18)

In a fashion similar to the preparation of 1, treatment of anhydrous copper(II) chloride (0.469 g, 3.49 mmol) in tetrahydrofuran (40 mL) with a solution of potassium 3-(isopropylimino)-2-methylbutan-2-olate (prepared from 3-(isopropylimino)-2-methylbutan-2-ol (1.000 g, 6.98 mmol) and potassium hydride (0.308 g, 7.68 mmol) in tetrahydrofuran (30 mL)) for 15 h at ambient temperature afforded 18 (0.857 g, 71%) as purple crystals upon sublimation at 90° C./0.05

Torr: mp 142-144° C.; IR (Nujol, cm$^{-1}$) 1633 ($v_{C=N}$, s); $\mu_{eff}$=1.61 and 1.80 BM in solid state and benzene solution, respectively.

Preparation of Bis(3-(2,2-dimethylhydrazono)-2-methylbutan-2-olate)nickel(II) (19)

In a fashion similar to the preparation of 1, treatment of anhydrous NiCl$_2$.CH$_3$CN (0.240 g, 1.25 mmol) in tetrahydrofuran (40 mL) with a solution of potassium 3-(2,2-dimethylhydrazono)-2-methylbutan-2-olate (prepared from 3-(2,2-dimethylhydrazono)-2-methylbutan-2-ol (0.360 g, 2.49 mmol) and potassium hydride (0.110 g, 2.74 mmol) in tetrahydrofuran (30 mL)) for 15 h at ambient temperature afforded 19 (0.331 g, 77%) as green crystals upon sublimation at 100° C./0.05 Torr: mp 160-162° C.; IR (Nujol, cm$^{-1}$) 1616 (m) 1341 (m) 1292 (w) 1260 (w) 1187 (s) 1135 (s) 1021 (s) 988 (s) 900 (w) 866 (w) 801 (w) 757 (w) 678 (m) 627 (w); $^1$H NMR (C$_6$D$_6$, 23° C., δ) 1.166 (s, 6H, OC (CH$_3$)$_2$), 1.500 (m, 3H, CCH$_3$), 2.770 (s, 6H, N(CH$_3$)$_2$); $^{13}$C {$^1$H} NMR (C$_6$D$_6$, 23° C., ppm) 197.201 (m, CO), 80.304 (m, C=N), 44.253 (s, N(CH$_3$)$_2$), 29.989 (s, OC(CH$_3$)$_2$), 14.950 (m, CCH$_3$).

Preparation of Bis(3-(2,2-dimethylhydrazono)-2-methylbutan-2-olate)cobalt(II) (20)

In a fashion similar to the preparation of 1, treatment of anhydrous cobalt(II) chloride (0.162 g, 1.24 mmol) in tetrahydrofuran (40 mL) with a solution of potassium 3-(2,2-dimethylhydrazono)-2-methylbutan-2-olate (prepared from 3-(2,2-dimethylhydrazono)-2-methylbutan-2-ol (0.360 g, 2.49 mmol) and potassium hydride (0.110 g, 2.74 mmol) in tetrahydrofuran (30 mL)) for 15 h at ambient temperature afforded 20 (0.258 g, 60%) as green crystals upon sublimation at 100° C./0.05 Torr: mp 142-143° C.; IR (Nujol, cm$^{-1}$) 1620 (m) 1260 (m) 1187 (s) 1133 (s) 1020 (s) 990 (m) 964 (m) 889 (w) 865 (w) 804 (m) 756 (w) 687 (w) 638 (w); $^1$H NMR (C$_6$D$_6$, 23° C., δ) 10.028 (s, broad); $\mu_{eff}$=1.57 and 3.10 BM in the solid state and benzene solution, respectively.

Preparation of Bis(3-(2,2-dimethylhydrazono)-2-methylbutan-2-olate)iron(II) (21)

In a fashion similar to the preparation of 1, treatment of anhydrous iron(II) chloride (0.158 g, 1.24 mmol) in tetrahydrofuran (40 mL) with a solution of potassium 3-(2,2-dimethylhydrazono)-2-methylbutan-2-olate (prepared from 3-(2,2-dimethylhydrazono)-2-methylbutan-2-ol (0.360 g, 2.49 mmol) and potassium hydride (0.110 g, 2.74 mmol) in tetrahydrofuran (30 mL)) for 15 h at ambient temperature afforded 21 (0.269 g, 63%) as green crystals upon sublimation at 100° C./0.05 Torr: mp 163-164° C.; IR (Nujol, cm$^{-1}$) 1617 (s) 1267 (m) 1185 (s) 1135 (s) 1091 (s) 996 (s) 881 (m) 845 (m) 744 (s) 614 (s) 539 (m); $^1$H NMR (CDCl$_3$, 23° C., δ) 2.451 (s, broad) 1.942 (m, broad) 1.253 (s, broad); $\mu_{eff}$=8.03 and [7.55 BM (dimer), 5.34(monomer)] in the solid state and benzene solution, respectively.

Preparation of Bis(3-(2,2-dimethylhydrazono)-2-methylbutan-2-olate)manganese(II) (22)

In a fashion similar to the preparation of 1, treatment of anhydrous manganese(II) chloride (0.157 g, 1.24 mmol) in tetrahydrofuran (40 mL) with a solution of potassium 3-(2, 2-dimethylhydrazono)-2-methylbutan-2-olate (prepared from 3-(2,2-dimethylhydrazono)-2-methylbutan-2-ol (0.360 g, 2.49 mmol) and potassium hydride (0.110 g, 2.74 mmol) in tetrahydrofuran (30 mL)) for 15 h at ambient temperature afforded 22 (0.226 g, 53%) as yellow crystals by crystallization at −23° C. in hexanes: mp 164-166° C.; IR (Nujol, cm-1) 1614 (s) 1261 (s) 1184 (s) 1129 (s) 1020 (s) 985 (s) 876 (m) 856 (w) 803 (m) 746 (m) 600 (m) 538 (w); 1H NMR (C6D6, 23° C., δ) 7.835 (s, broad) 2.979 (w, broad) 2.025 (w, broad); $\mu_{eff}$=8.54(dimer) 6.03(monomer) and [7.92 BM (dimer), 5.60(monomer)] in the solid state and benzene solution, respectively.

Preparation of Bis(3-(2,2-dimethylhydrazono)-2-methylbutan-2-olate)chrolium(II) (23)

In a fashion similar to the preparation of 1, treatment of anhydrous chromium(II) chloride (0.153 g, 1.24 mmol) in tetrahydrofuran (40 mL) with a solution of potassium 3-(2, 2-dimethylhydrazono)-2-methylbutan-2-olate (prepared from 3-(2,2-dimethylhydrazono)-2-methylbutan-2-ol (0.360 g, 2.49 mmol) and potassium hydride (0.110 g, 2.74 mmol) in tetrahydrofuran (30 mL)) for 15 h at ambient temperature afforded 23 (0.205 g, 49%) as dark red crystals upon sublimation at 90° C./0.05 Torr:: mp 144-146° C.; IR (Nujol, cm$^{-1}$) 1615 (m) 1261 (w) 1187 (s) 1133 (s) 1098 (m) 1018 (m) 991 (s) 889 (w) 860 (w) 802 (w) 750 (w) 722 (w) 678 (w) 633 (m) 579 (w) 550 (w) 534 (w); $^1$H NMR (C$_6$D$_6$, 23° C., δ) 2.249 (s, broad) 2.210 (w, broad) 2.006 (w, broad) 1.645 (m, broad) 1.374 (m, broad) 1.248 (s, broad) 0.926 (w, broad); $\mu_{eff}$=4.84 and 4.88 BM in the solid state and benzene solution, respectively.

Preparation of Bis(3-(2,2-dimethylhydrazono)-2-methylbutan-2-olate)copper(II) (24)

In a fashion similar to the preparation of 1, treatment of anhydrous copper(II) chloride (0.466 g, 3.49 mmol) in tetrahydrofuran (40 mL) with a solution of potassium 3-(2, 2-dimethylhydrazono)-2-methylbutan-2-olate (prepared from 3-(2,2-dimethylhydrazono)-2-methylbutan-2-ol (1.000 g, 6.93 mmol) and potassium hydride (0.306 g, 7.63 mmol) in tetrahydrofuran (30 mL)) for 15 h at ambient temperature afforded 24 (0.991 g, 75%) as purple crystals upon sublimation at 80° C./0.05 Torr: mp 150-153° C.; IR (Nujol, cm$^{-1}$) 1627 ($v_{C=N}$, s); $\mu_{eff}$=1.58 and 1.25 BM in solid state and benzene solution, respectively.

Figure 3A:
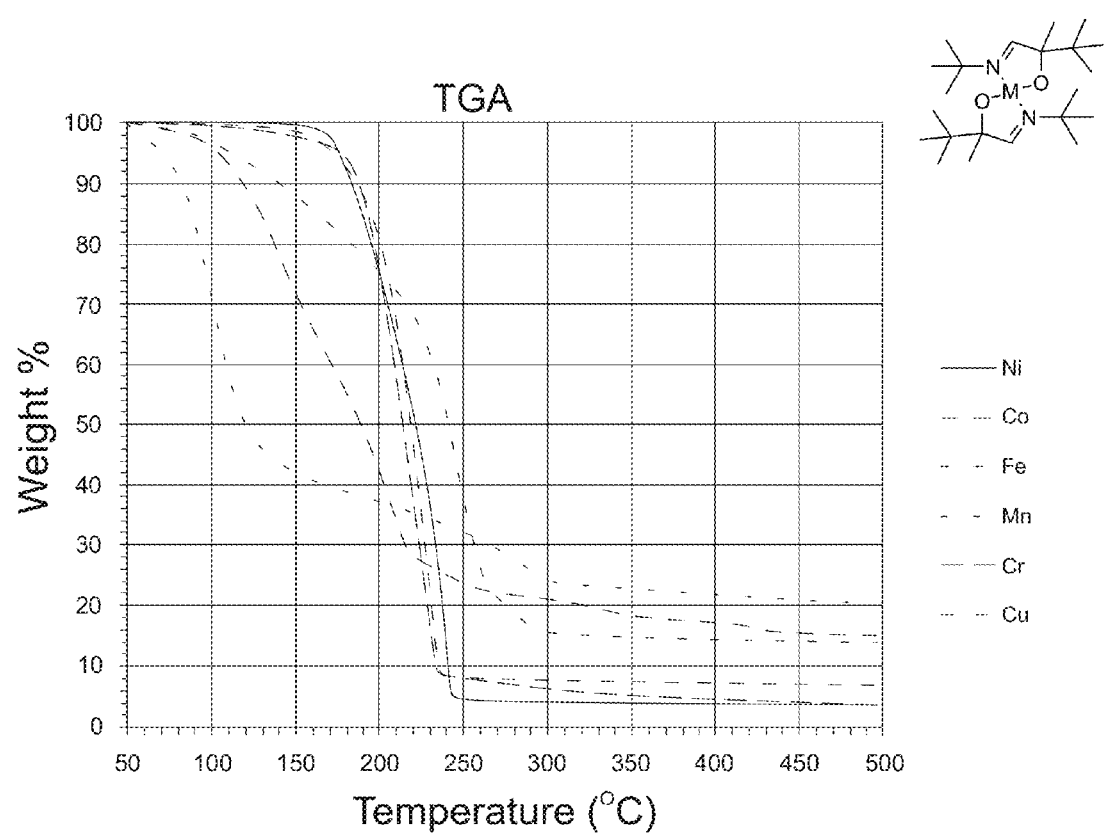
FIG. 3A provides thermogravimetic analysis (TGA) traces for complexes 1-6.
Figure 3B:
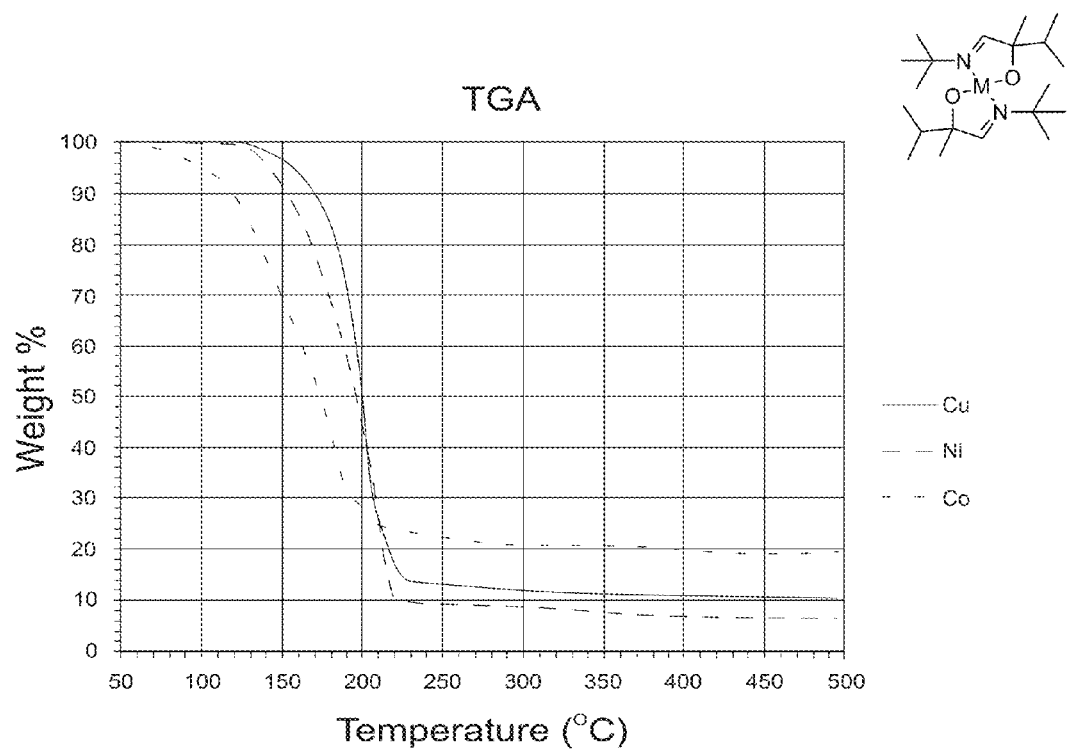
FIG. 3B provides TGA traces for complexes 7, 8, and 10.
Figure 3C:
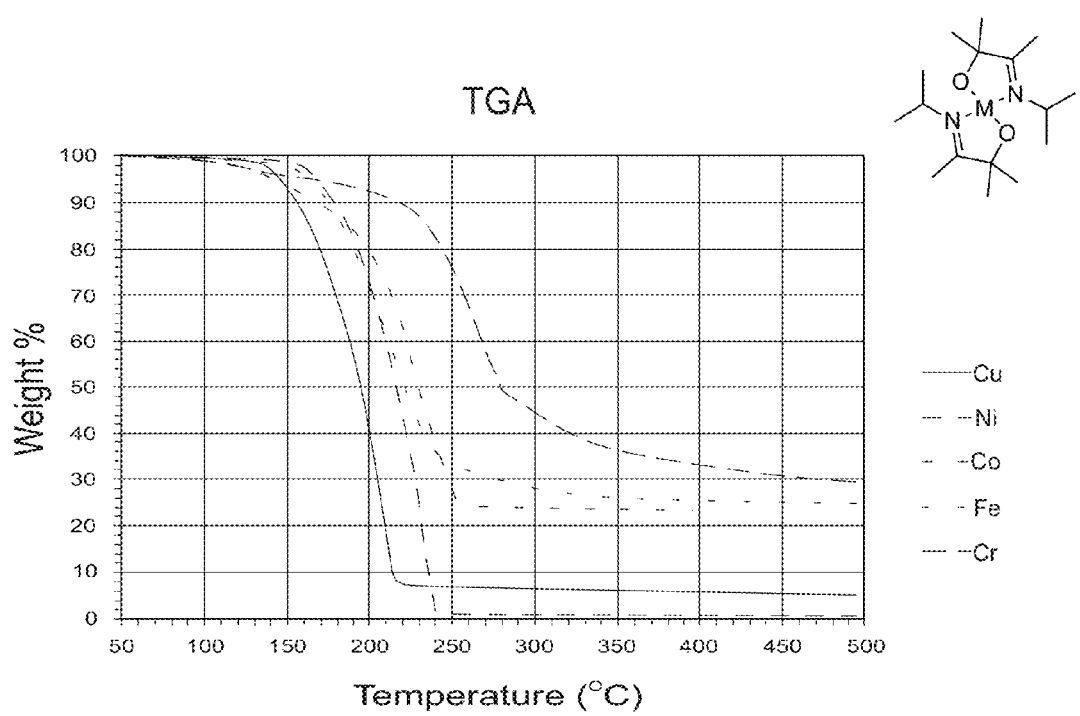
FIG. 3C provides TGA traces for complexes 13-18.
Figure 3D:
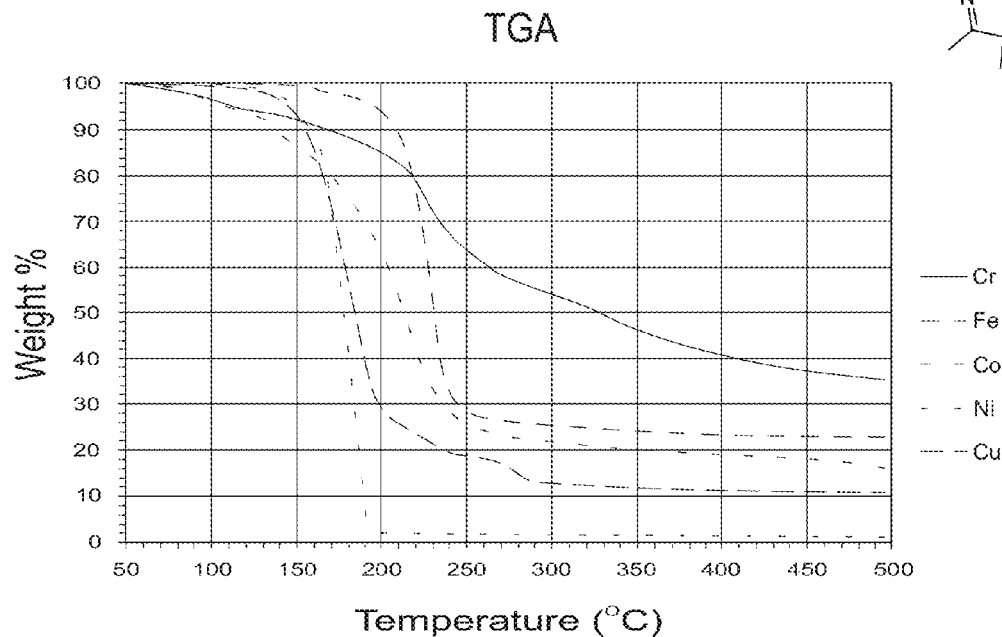
FIG. 3D provides TGA traces for complexes 19-24.
Figure 3D:
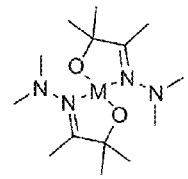

Tables 1 and 2 provide thermal and volatility properties for complexes 1-24 demonstrating sufficient properties for the complexes to be useable in ALD processes. Tables 3-6 provide information regarding selected complexes with various reducing agents. FIG. 3A-B provide TGA results for various complexes.

TABLE 1

Thermal and volatility properties of 1-12.

| Complex | Sublimation temperature (° C./0.05 Torr) | Melting point (° C.) | Solid state decomposition temperature (° C.) | % Recovery | % Non-volatile residue |
|---|---|---|---|---|---|
| 1 | 120 | 175-177 | 231 | 96 | 3 |
| 2 | 115 | 84-86 | 232 | 96 | 2 |
| 3 | 85 | 112-114 | 246 | 96 | 3 |
| 4 | 160 | 220-223 | 259 | 95 | 3 |
| 5 | 115 | 173-175 | 230 | 95 | 3 |
| 6 | 130 | 163-165 | 203 | 97 | 3 |
| 7 | 90 | 125-127 | 216 | 96 | 3 |
| 8 | 90 | 96-98 | 234 | 97 | 2 |

TABLE 1-continued

Thermal and volatility properties of 1-12.

| Complex | Sublimation temperature (° C./0.05 Torr) | Melting point (° C.) | Solid state decomposition temperature (° C.) | % Recovery | % Non-volatile residue |
|---|---|---|---|---|---|
| 9 | 75 | 92-94 | — | — | — |
| 10 | 105 | 134-136 | 183 | 97 | 3 |
| 11 | 130 | — | — | — | — |
| 12 | 135 | 183-185 | 185 | 97 | 3 |

TABLE 2

Thermal and volatility properties of 13-24.

| Complex | Sublimation temperature (° C./0.05 Torr) | Melting point (° C.) | Solid state decomposition temperature (° C.) | % Recovery |
|---|---|---|---|---|
| 13 | 100 | 158-160 | 255 | 98 |
| 14 | 90 | 144-146 | 255 | 50 |
| 15 | 180 | 172-175 | 285 | — |
| 16 | 170 | 202-203 | 240 | — |
| 17 | 90 | 143-146 | 205 | 79 |
| 18 | 90 | 142-144 | 185 | 98 |
| 19 | 80 | 160-162 | 230 | 98 |
| 20 | 100 | 142-143 | 205 | 85 |
| 21 | — | 163-164 | 210 | — |
| 22 | — | 164-466 | 230 | — |
| 23 | 90 | 144-146 | 146 | 74 |
| 24 | 80 | 150-153 | 180 | 97 |

TABLE 3

Reactivity of 4 toward reducing agents.

| Reducing agent | Observation |
|---|---|
| $BH_3 \cdot NEt_3$ | No change |
| $BH_3 \cdot NHMe_2$ | Black powder when refluxed |
| $BH_3 \cdot THF$ | No change |
| $LiBHEt_3$ | No change |
| 9-BBN | No change |
| $NH_2NMe_2$ | No change |
| $AlEt_3$ | Black powder at r.t. |
| $AlMe_3$ | Black powder at r.t. |
| $LiAlH_4$ | Black powder at r.t. |
| $HSiEt_3$ | No change |

TABLE 4

Reactivity of 1, 2, 7, and 8 toward reducing agents.

| Reducing agent | 1 | 2 | 7 | 8 |
|---|---|---|---|---|
| $NH_2NH_2$ | Black, magnetic powder | Black, magnetic powder | Black, magnetic powder | Black, magnetic powder |
| $BH_3 \cdot NHMe_2$ | Black, magnetic powder | Black, magnetic powder | Black, magnetic powder | Black, magnetic powder |

TABLE 5

Reactivity of 13, 14, and 17 toward reducing agents.

| Reducing agent | 13 | 14 | 17 |
|---|---|---|---|
| $NH_2NH_2$ | Black, magnetic powder | Metallic, magnetic precipitate | Pink |
| $NH_2NMe_2$ | Turned Red | — | No Change |
| $BH_3 \cdot THF$ | Black powder | — | — |
| $BH_3 \cdot NHMe_2$ | — | Black powder | — |

TABLE 6

Reactivity of 19, 20, 22 and 23 toward reducing agents.

| Reducing agent | 19 | 20 | 22 | 23 |
|---|---|---|---|---|
| $NH_2NH_2$ | Black, magnetic powder | Metallic, magnetic deposit | Light blue | Pink |
| $NH_2NMe_2$ | No change | No change | No change | — |
| $LiBHEt_3$ | — | — | Pink | — |
| $BH_3 \cdot THF$ | Black powder | Brown | Brown | Brown |
| $HN(CH_3)_2 \cdot BH_3$ | — | Black powder | — | — |

ALD Studies Using α-imino Alkoxide Precursors

Overview.

ALD studies have been done using precursors, 4, 5, 7, and 8 with $BH_3.NHMe_2$ and hydrazine. ALD of 5, 7, and 8 with $BH_3.NHMe_2$ afforded corresponding metal films according to XPS data. (Cobalt, Nickel, Chromium). ALD of compound 4 with $BH_3.NHMe_2$ afforded $MnO_2$ according to XPS data. However these films are exposed to air before XPS is done. Therefore, Mn film deposited may have been oxidized in air to $MnO_2$. ALD of 7 and 8 with hydrazine afforded corresponding nitride films according to XPS data. Thicknesses as determined by scanning electron microscopy (SEM) images include ruthenium thickness ~5 nm.

1. ALD Studies of 4 [$Mn_2(tBuMeCOCNtBu)_4$] with $BH_3.NHMe_2$

Figure 4:
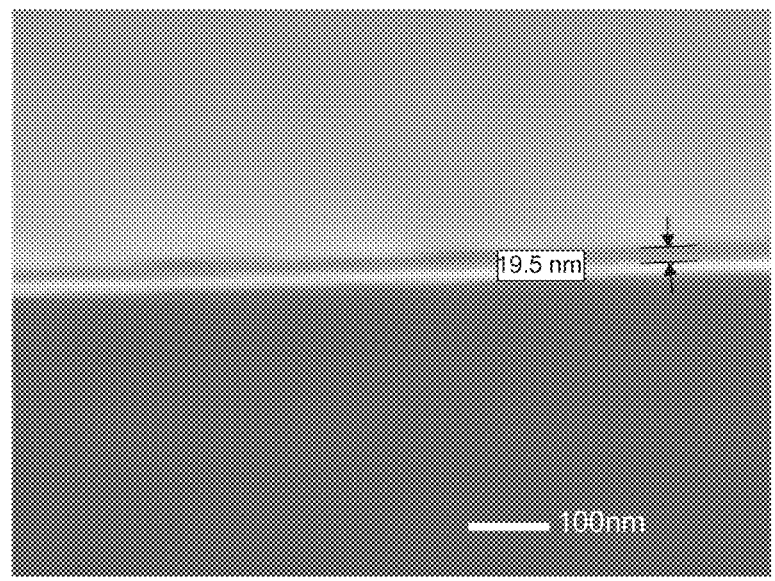
FIG. 4 provides an SEM of a manganese-containing film deposited by ALD on a Ru/SiO$_2$ substrate at 225° C. by reacting a Mn imino alkoxide with BH$_3$NHMe$_2$.
Figure 5:
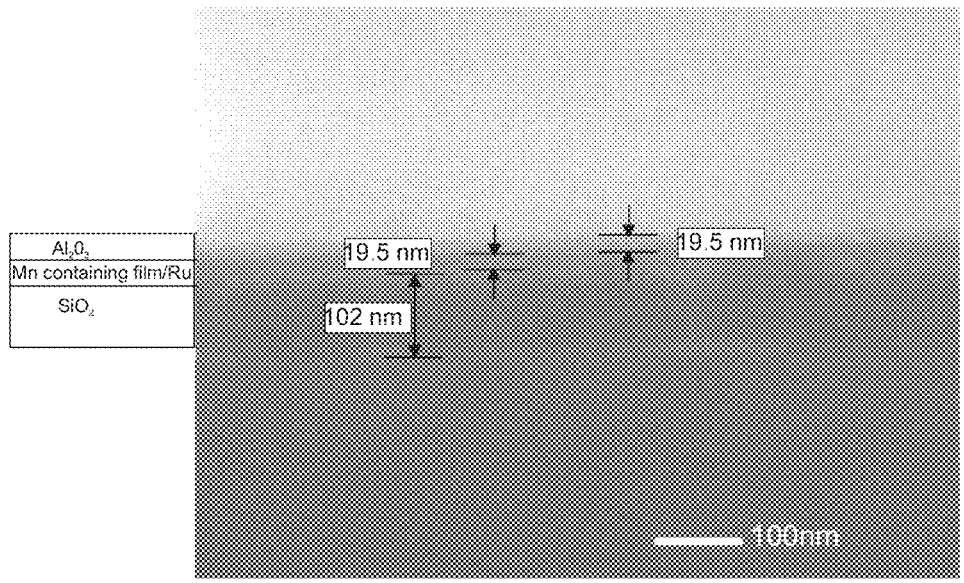
FIG. 5 provides an SEM of a manganese-containing film as in FIG. 1 over-coated with an aluminum oxide film.
Figure 6:
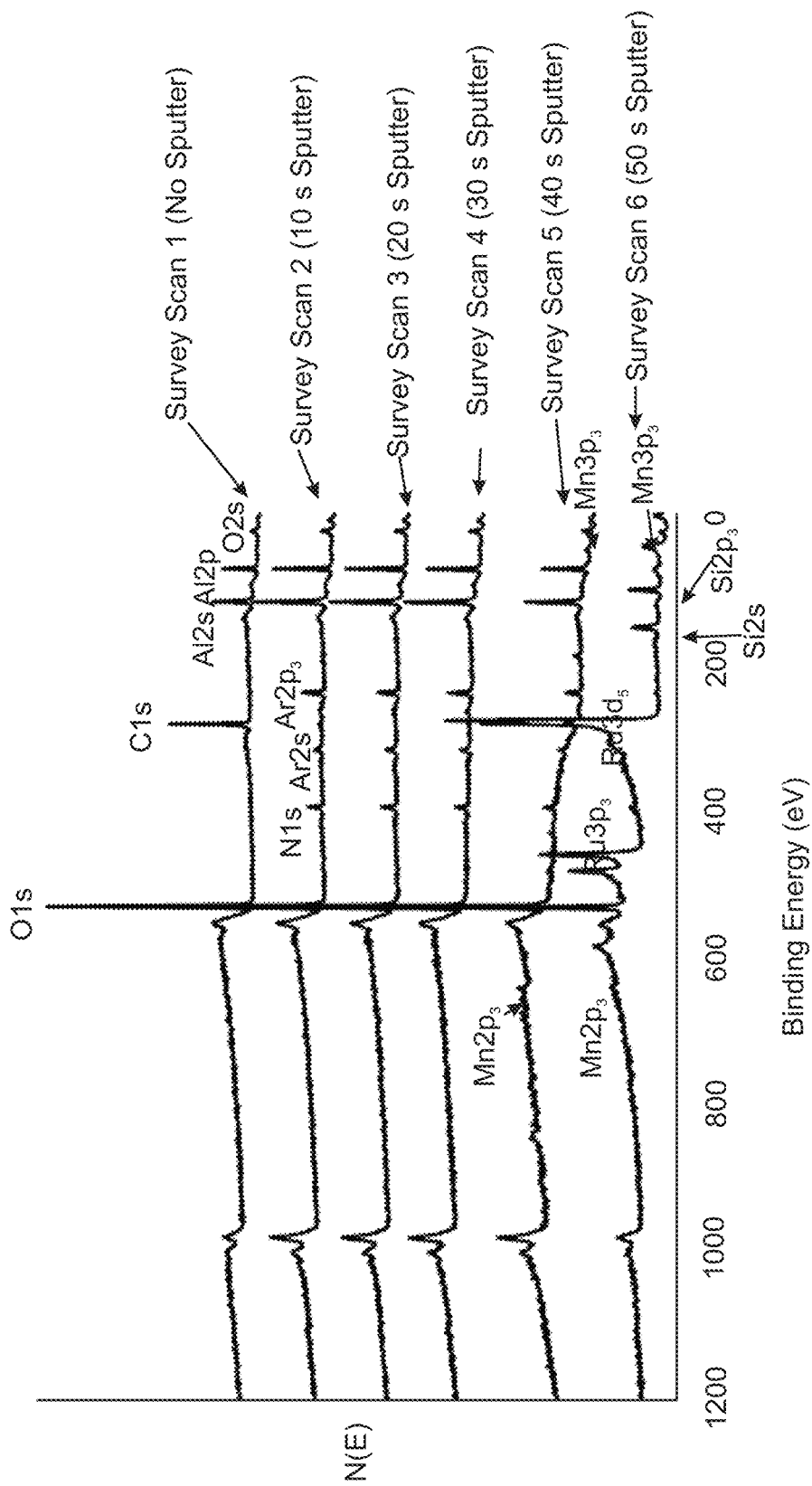
FIG. 6 is an XPS spectrum of a manganese-containing film deposited by ALD on a Ru/SiO$_2$ substrate at 225° C. by reacting a Mn imino alkoxide with BH$_3$NHMe$_2$.
Figure 7:
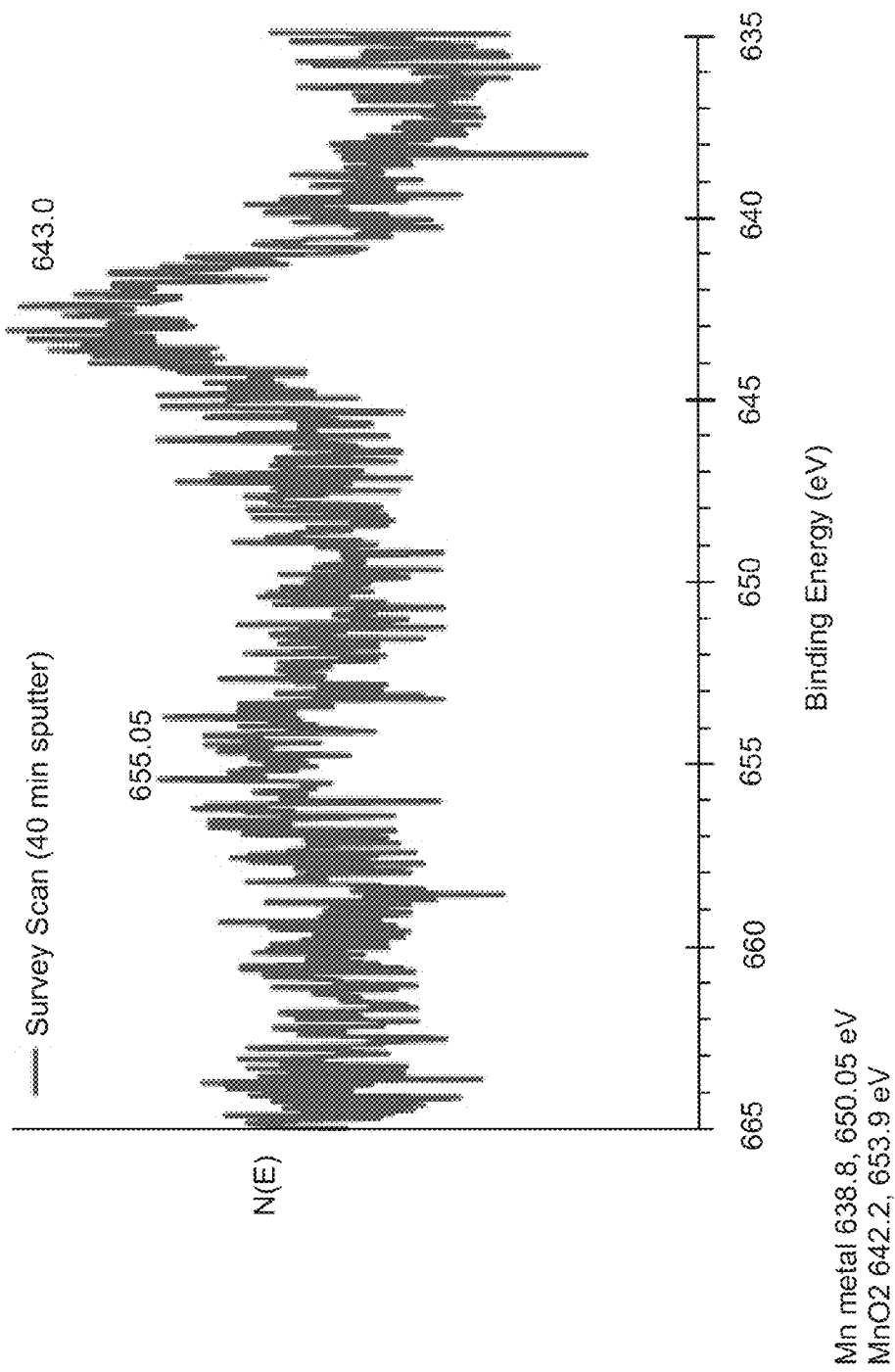
FIG. 7 is a high resolution XPS spectrum of a manganese-containing film deposited by ALD on a Ru/SiO$_2$ substrate at 225° C. by reacting a Mn imino alkoxide with BH$_3$NHMe$_2$.

A manganese containing film was deposited in accordance with the following conditions. In a nucleation cycle, 50 cycles were run with Mn precursor 4 pulse time of 20.0 seconds (s), Mn precursor purge time 5.0 s, $BH_3.NHMe_2$ pulse time of 1.0, $BH_3.NHMe_2$ purge time 10.0 s. In a film deposition step, 2000 cycles were run with Mn Precursor 4 pulse time of 3.0 s, Mn precursor purge time 5.0, $BH_3.NHMe_2$ pulse time of 1.0 s, and $BH_3.NHMe_2$ purge time 10.0 s. Film coatings were prepared on a $Ru/SiO_2$ substrate at a substrate temperature of 225° C., Mn precursor temperature of 180° C., borane precursor temperature of 80° C. A Mn containing film was deposited at a thickness of about 19.5 nm. In a separate run, the same film was overcoated with ALD $Al_2O_3$ (19.5 nm, 300 cycles) using TMA and water at 225° C. No features observed in surface SEM (FIGS. 4 and 5). FIG. 6 is an X-Ray Photoelectron (XPS) spectroscopy plot of a Mn-containing film. FIG. 7 is a high resolution XPS spectrum.

2. ALD Studies of 5 [$Cr(tBuMeCOCNtBu)_2$] with $BH_3.NHMe_2$

Figure 8:
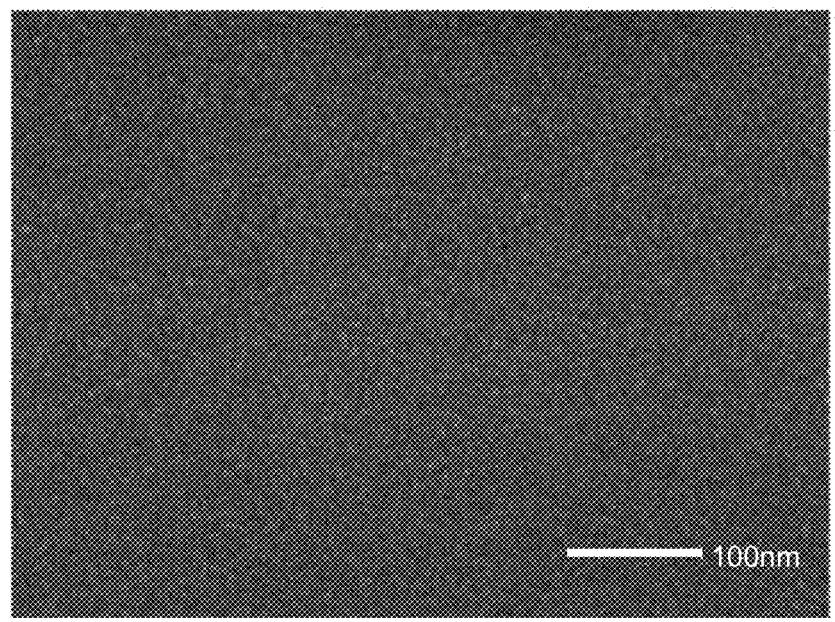
FIG. 8 provides an SEM top view image of a chromium film deposited by ALD on a Ru substrate at 180° C.
Figure 9:
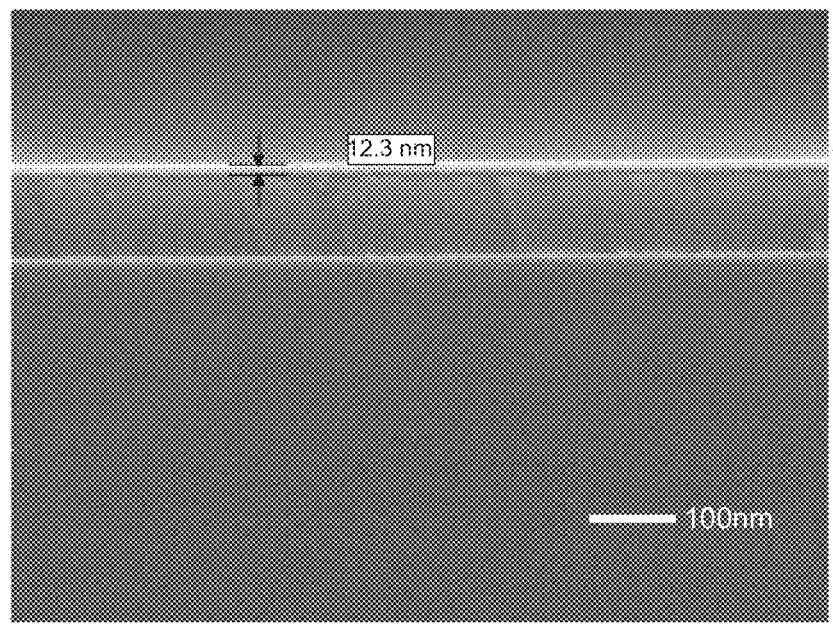
FIG. 9 provides an SEM cross sectional view of a chromium film deposited by ALD on a ruthenium substrate at 180° C.
Figure 10:
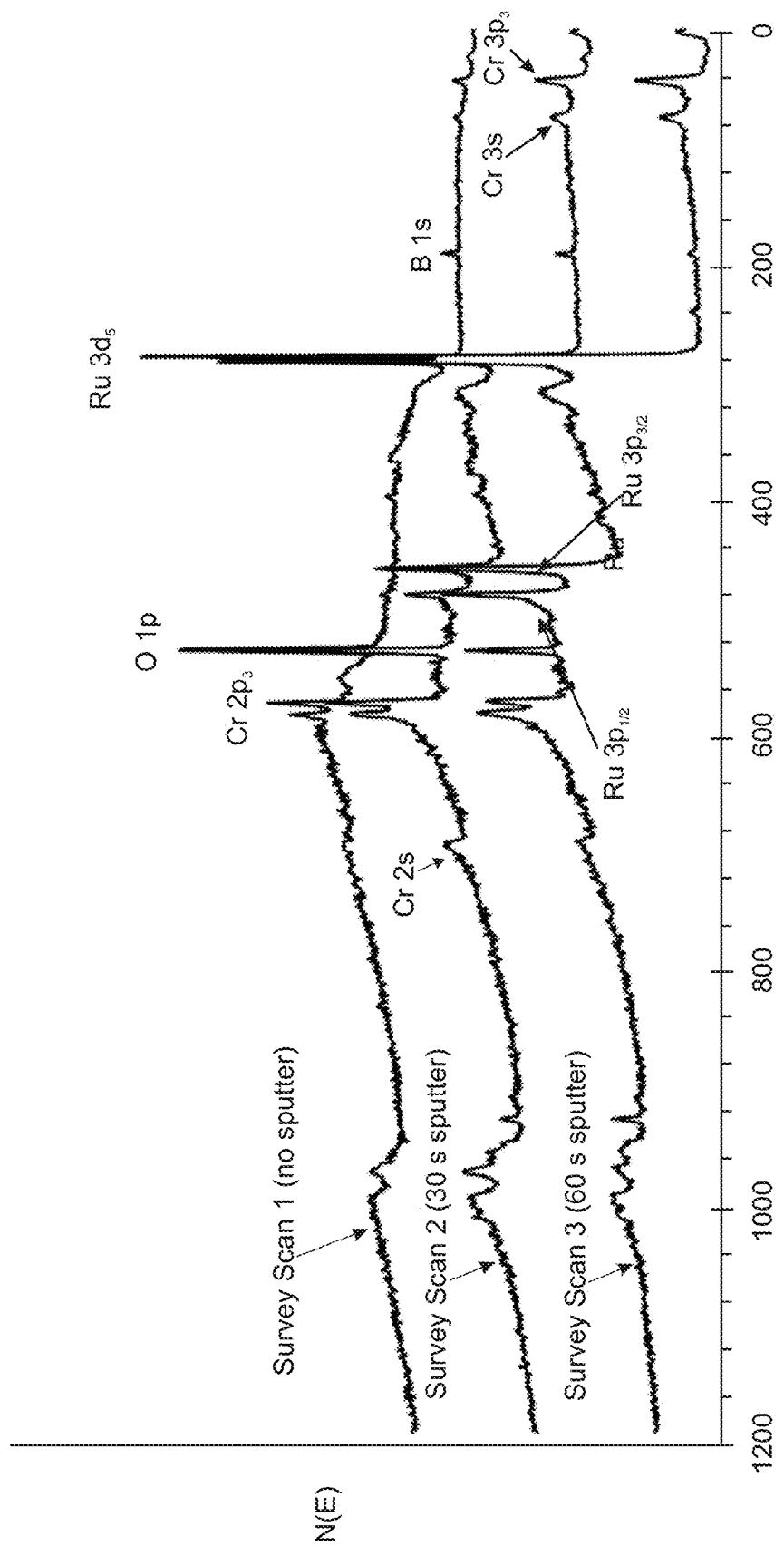
FIG. 10 is an XPS spectrum of an 8 nm thick chromium film deposited by ALD on a ruthenium substrate at 180° C.
Figure 11:
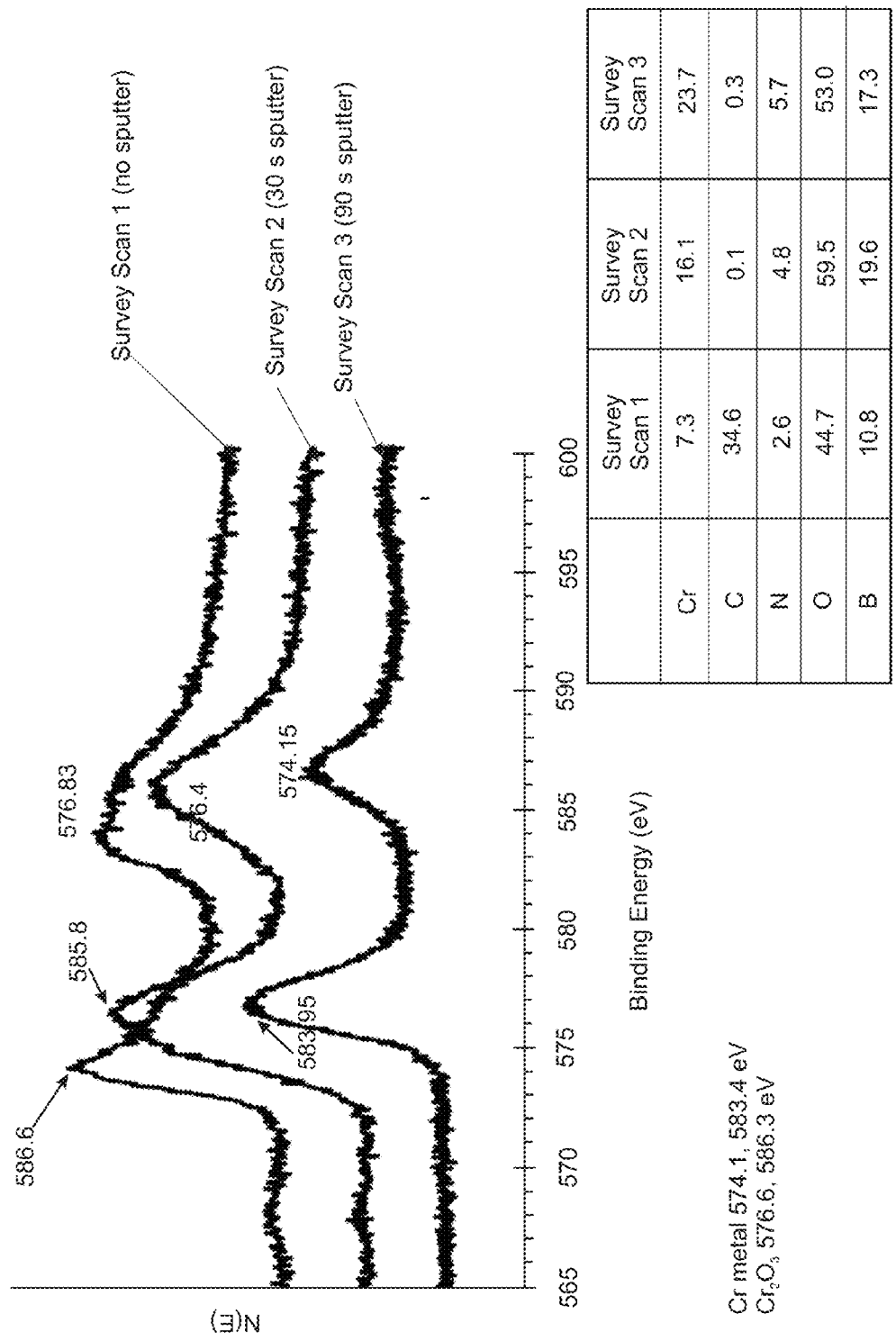
FIG. 11 is a high resolution multiplexed XPS spectrum of an 8 nm thick chromium film deposited by ALD on a ruthenium substrate at 180° C.

A chromium containing film was deposited in accordance with the following conditions. In a nucleation cycle, 50 cycles were run with a Cr(tBuMeCOCNtBu)$_2$ pulse time of 20.0 s Cr(tBuMeCOCNtBu)$_2$ purge time 5.0 s, BH$_3$.NHMe$_2$ pulse time of 1.0 s, and BH$_3$.NHMe$_2$ purge time 10.0 s. In a film growth step, 1000 cycles were run with Cr(tBuMeCOCNtBu)$_2$ pulse time of 3.0 s, Cr(tBuMeCOCNtBu)$_2$ purge time 5.0 s, BH$_3$.NHMe$_2$ pulse time of 1.0 s, BH$_3$.NHMe$_2$ purge time 10.0 s. Coatings were prepared on Ru, Pt, Pd, Si with native oxide, and on H-terminated Si substrates with a substrate temperature of about 180° C., Cr precursor temperature of about 140° C., and borane temperature of about 80° C. The films on Ru were visually gray in color. FIGS. 8 and 9 provide SEM images of chromium films on Ru. The thickness of the film was about 8 nm. FIGS. 10 and 11 provide XPS spectra which suggests that the film is chromium metal.

3. ALD Studies of 7 [Ni(iPrMeCOCNtBu)$_2$] with BH$_3$.NHMe$_2$.

Figure 12:
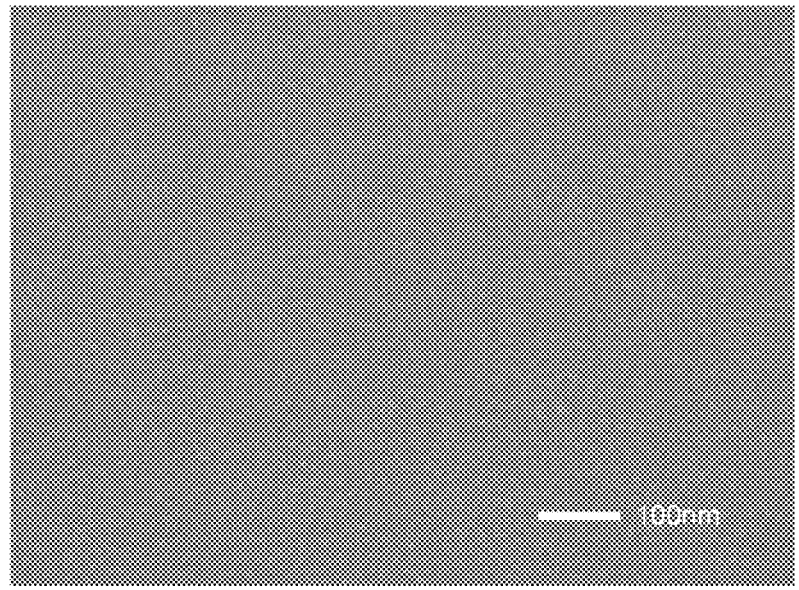
FIG. 12 provides an SEM top view of a nickel film deposited by ALD on a Ru/SiO$_2$ substrate at 180° C.
Figure 13:
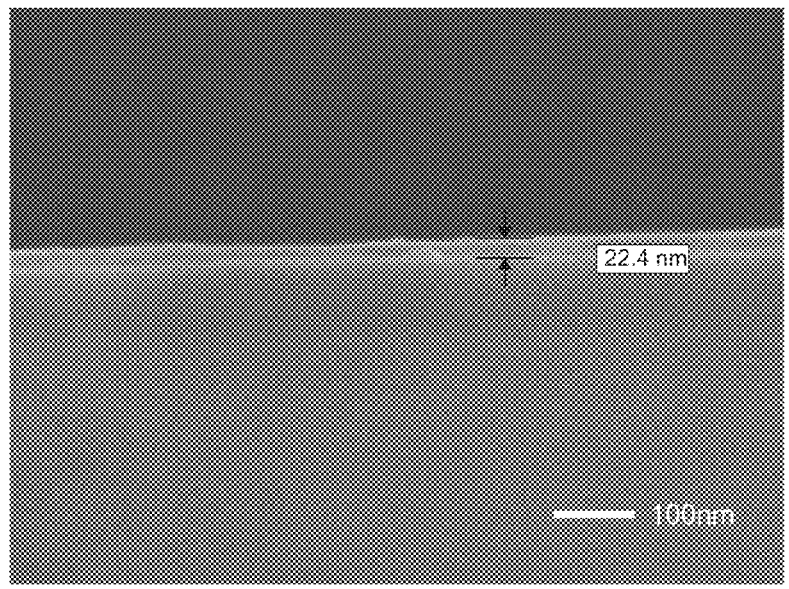
FIG. 13 provides an SEM cross sectional view of a nickel film deposited by ALD on a Ru/SiO$_2$ substrate at 180° C.
Figure 14:
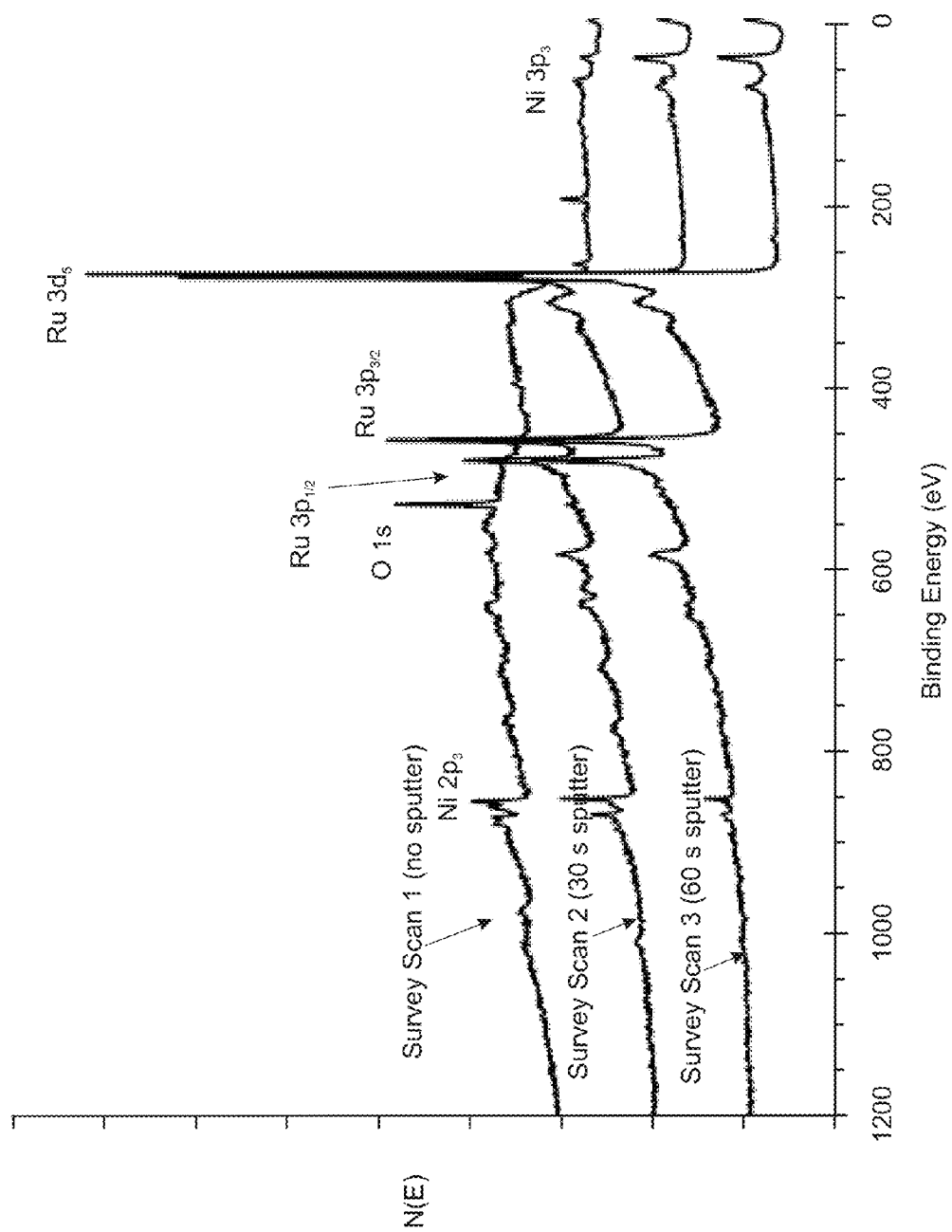
FIG. 14 is an XPS spectrum of a 17 nm nickel film deposited by ALD on a Ru/SiO$_2$ substrate at 180° C.
Figure 15:
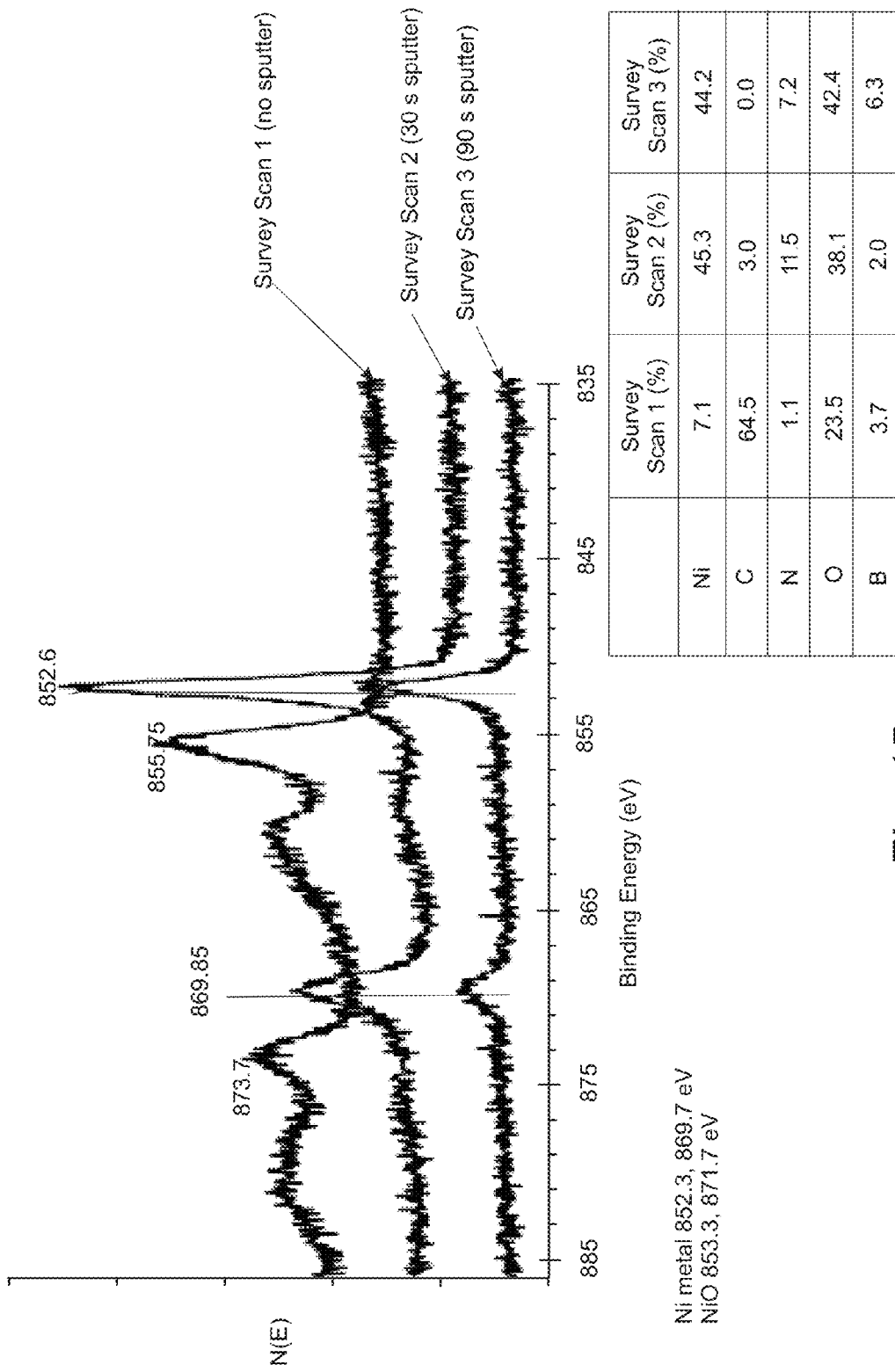
FIG. 15 is a high resolution multiplexed XPS spectrum of a 17 nm nickel film deposited by ALD on a Ru/SiO$_2$ substrate at 180° C.

A nickel-containing film was deposited in accordance with the following conditions. In a nucleation cycle, 50 cycles were run with a [Ni(iPrMeCOCNtBu)$_2$] pulse time of 20.0 s, Ni Precursor purge time of 5.0 s, a BH$_3$.NHMe$_2$ pulse time of 1.0 s, and a BH$_3$.NHMe$_2$ purge time of 10.0 s. In a film growth step, 1000 cycles were run with a Ni Precursor pulse time of 3.0 s, Ni Precursor purge time 5.0 s, BH$_3$.NHMe$_2$ pulse time of 1.0 s, and BH$_3$.NHMe$_2$ purge time 10.0 s. Films were deposited on Ru, Pd, Pt, Si substrates with native oxide, and on H-terminated Si substrates with a substrate temperature of about 180° C., Ni precursor temperature of about 120° C., borane precursor temperature of about 80° C. The films on Ru/SiO$_2$ were visually gray in color. FIGS. 12 and 13 provide SEM images of the deposited films. Typically, the films have a thickness of about 17 nm. FIGS. 14 and 15 provide XPS spectra confirming that the deposited film is nickel metal.

4. ALD Studies of 7 [Ni(iPrMeCOCNtBu)2] with Hydrazine.

Figure 16:
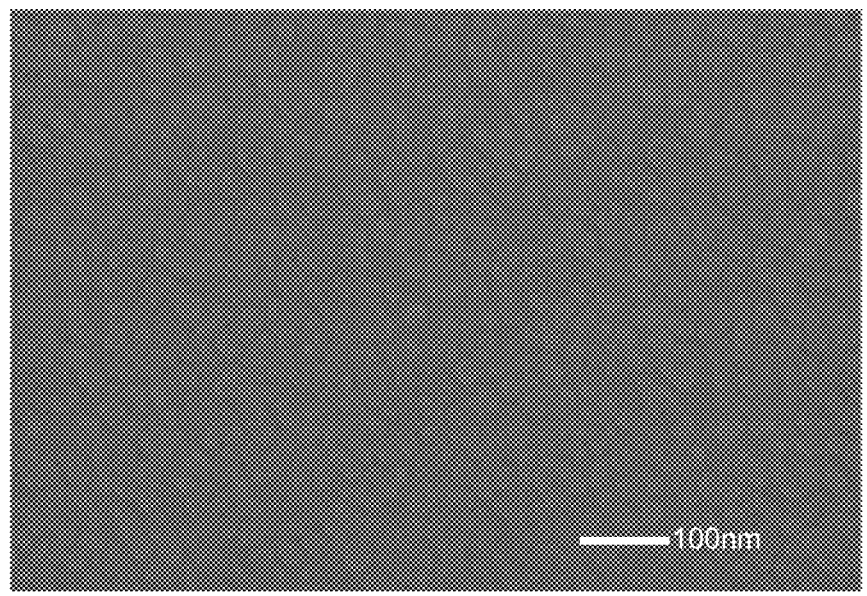
FIG. 16 provides an SEM top view of a nickel nitride film deposited by ALD on a Ru/SiO$_2$ substrate at 180° C. by reacting a nickel amino alkoxide with hydrazine.
Figure 17:
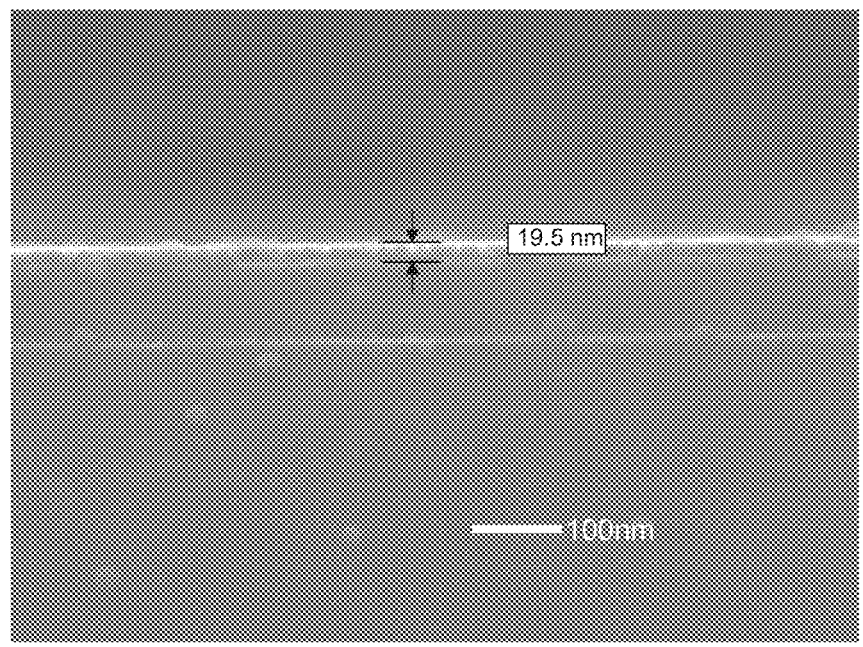
FIG. 17 provides an SEM cross sectional view of a nickel nitride film deposited by ALD on a Ru/SiO$_2$ substrate at 180° C. by reacting a nickel amino alkoxide with hydrazine.
Figure 18:
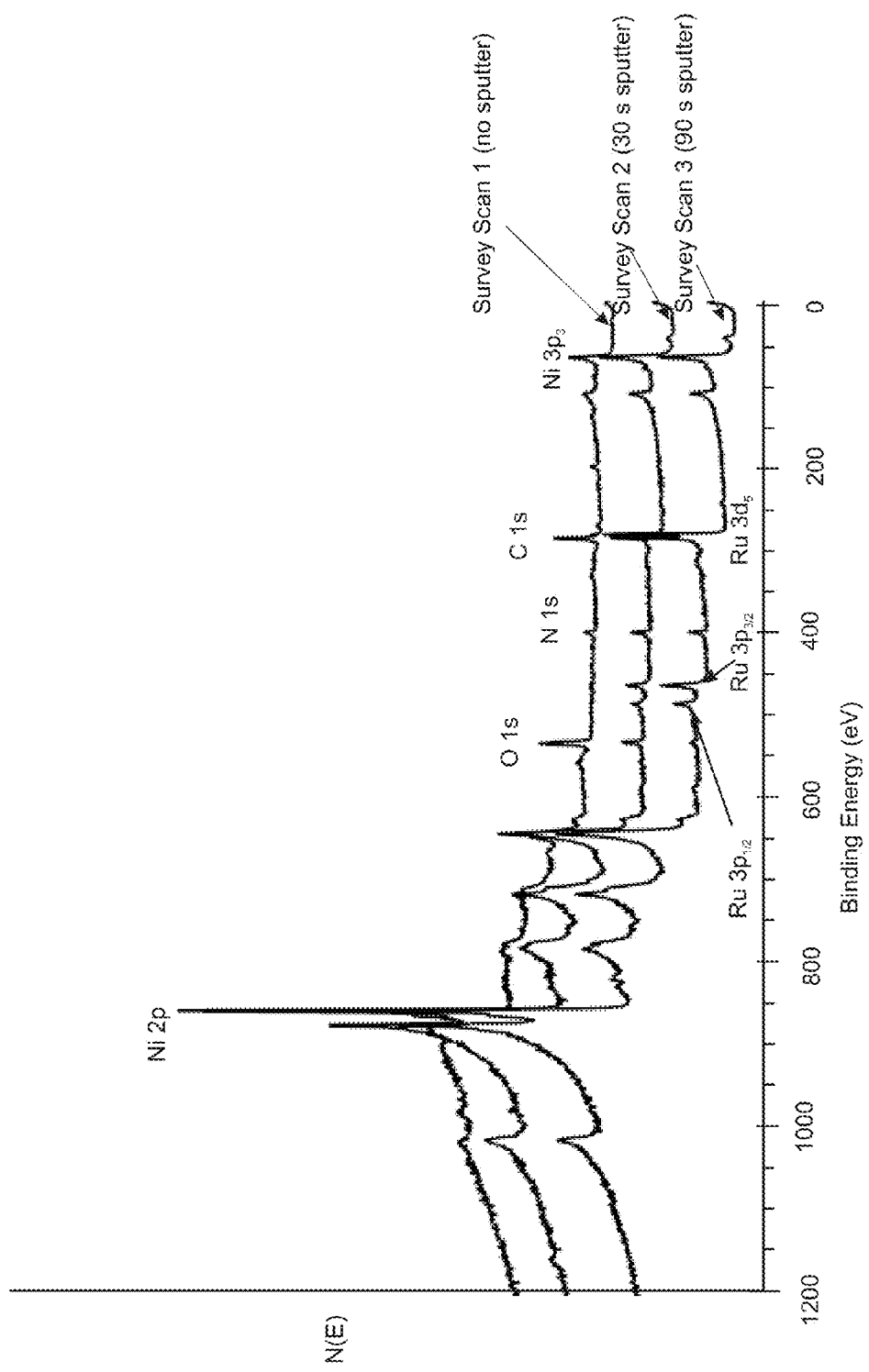
FIG. 18 is an XPS spectrum of a 15 nm nickel nitride film deposited by ALD on a Ru/SiO$_2$ substrate at 180° C. by reacting a nickel amino alkoxide with hydrazine.
Figure 19:
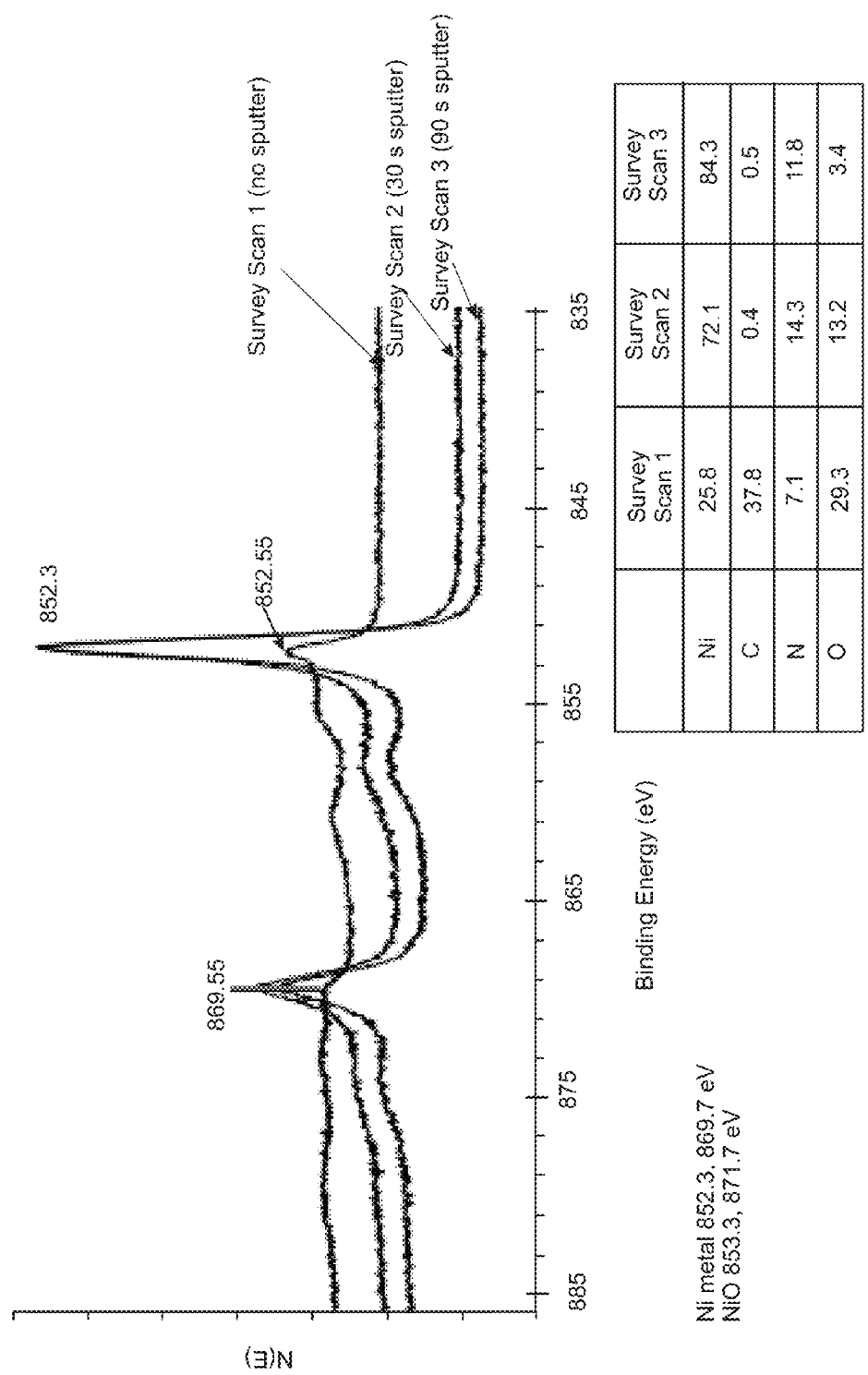
FIG. 19 is a high resolution multiplexed XPS spectrum of a 15 nm nickel nitride film deposited by ALD on a Ru/SiO$_2$ substrate at 180° C. by reacting a nickel amino alkoxide with hydrazine.

A nickel-containing film was deposited in accordance with the following conditions. In a film growth step, 1000 cycles were run with a Ni precursor pulse time of 3.0 s, Ni precursor purge time 5.0 s, N$_2$H$_4$ pulse time of 0.4 s, and N$_2$H$_4$ purge time 5.0 s. Films were deposited on Ru, Pd, Pt, Si substrates with native oxide, and on H-terminated Si substrates with a substrate temperature of 180° C. The films on Ru/SiO$_2$ were visually gray in color. FIGS. 16 and 17 provide SEM images of the deposited films. Typically, the films have a thickness of about 15 nm. FIGS. 18 and 19 provide XPS spectra confirming that the deposited film is nickel nitride.

5. ALD Studies of 8 [Co(iPrMeCOCNtBu)$_2$] with BH$_3$.NHMe$_2$

Figure 20:
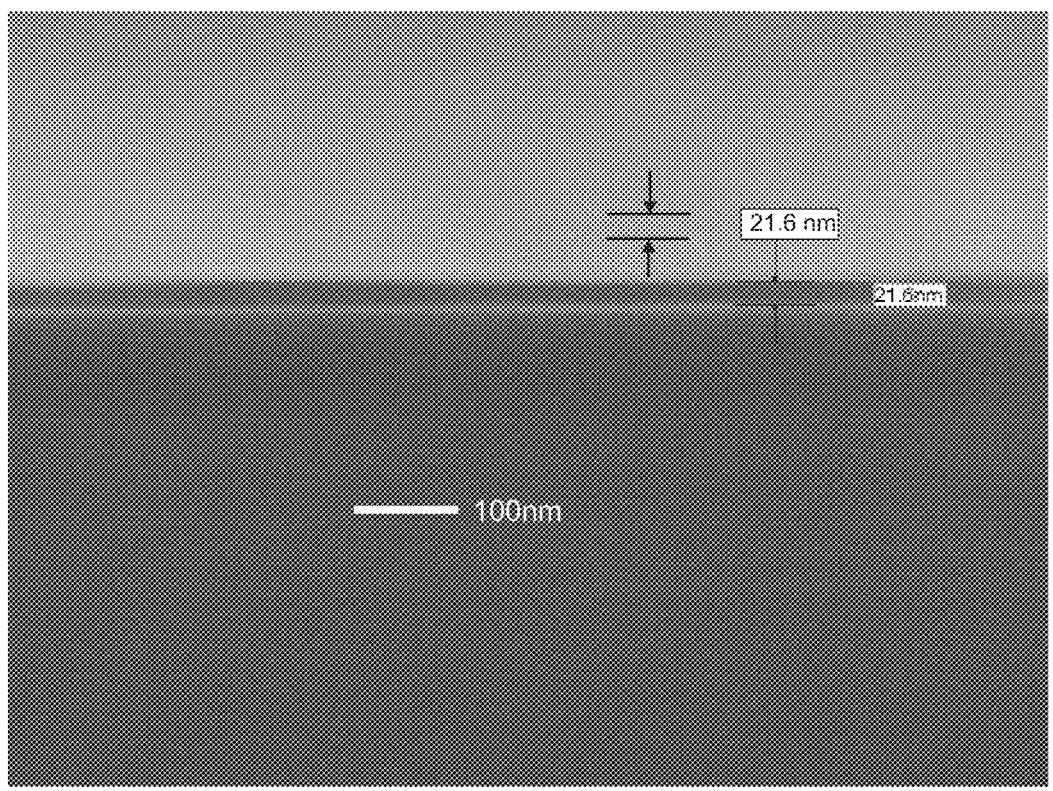
FIG. 20 provides an SEM cross section of a cobalt metal film deposited by ALD on a Ru/SiO$_2$ substrate at 180° C.
Figure 21:
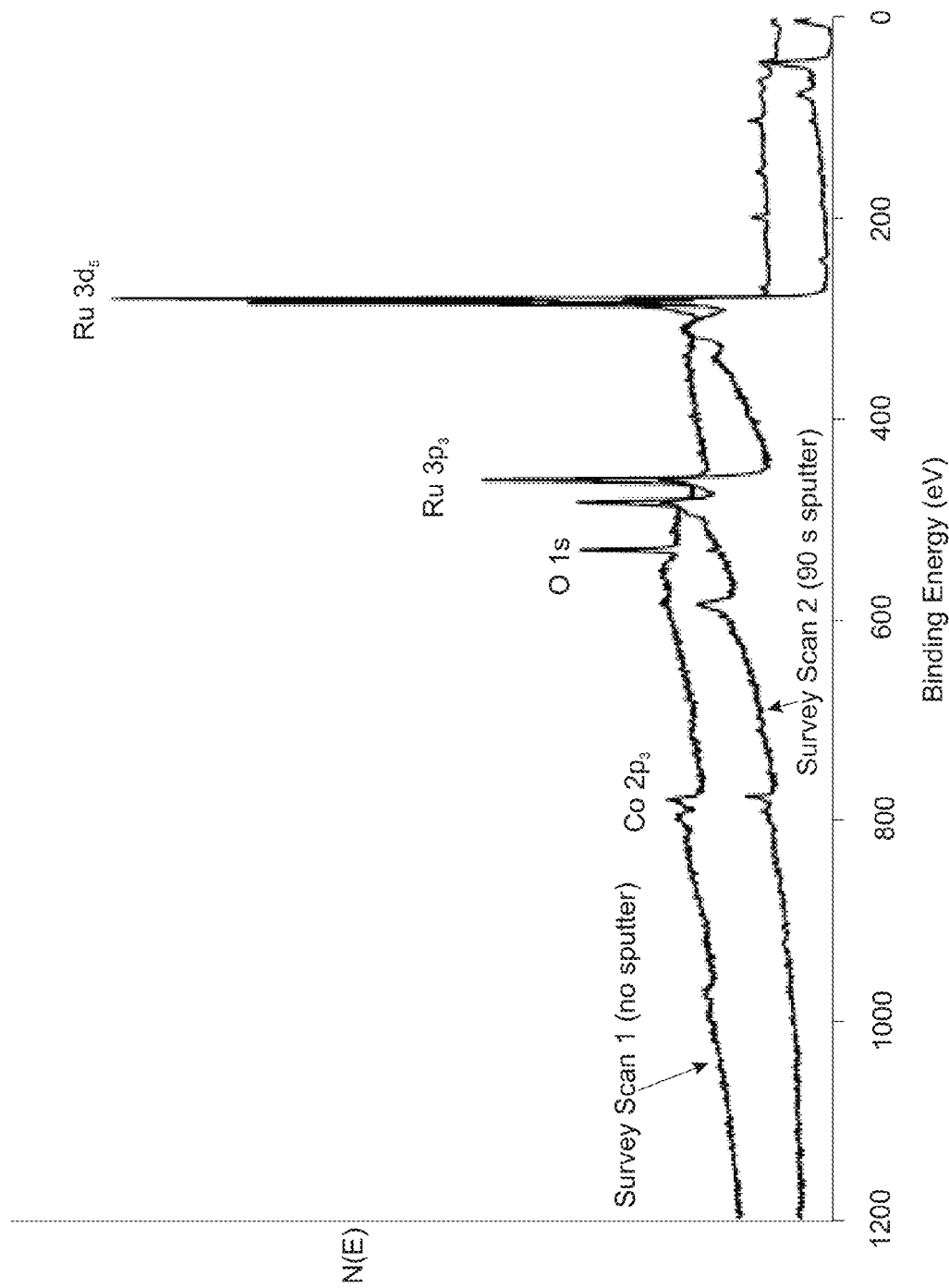
FIG. 21 provides an XPS spectrum of a 17 nm cobalt metal film deposited by ALD on a Ru/SiO$_2$ substrate at 180° C.
Figure 22:
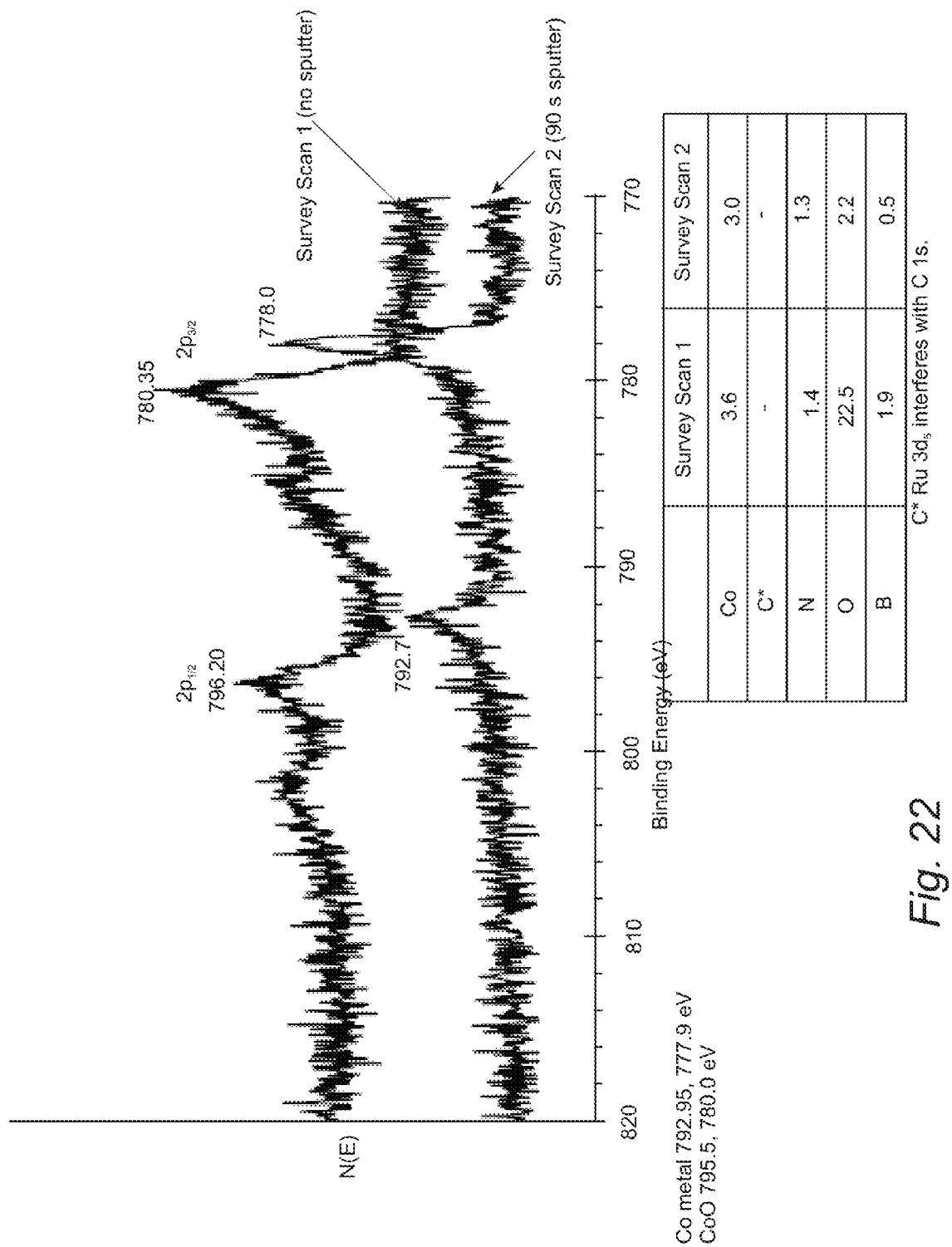
FIG. 22 provides a high resolution of a multiplexed XPS spectrum of a 17 nm cobalt metal film deposited on ALD on a Ru/SiO$_2$ substrate at 180° C.
Figure 23:
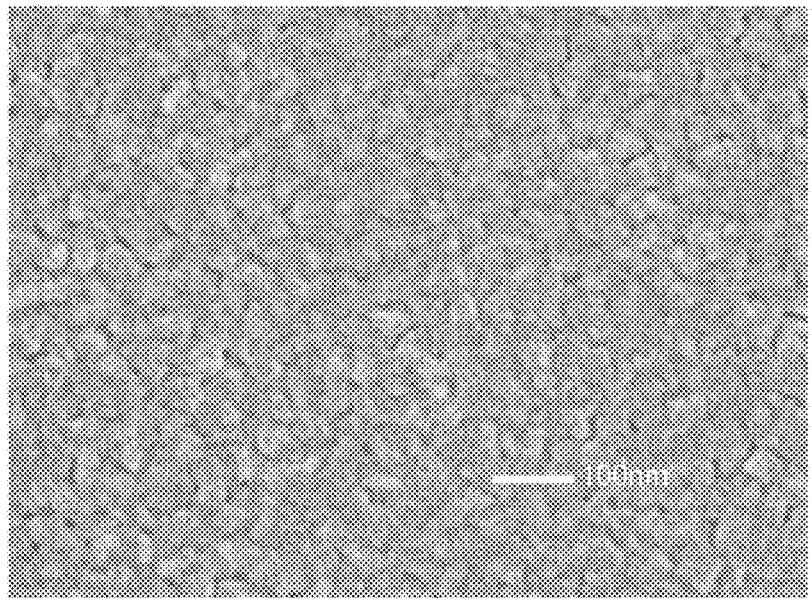
FIG. 23 provides an SEM top view of a cobalt nitride film deposited by ALD on a Ru/SiO$_2$ substrate at 180° C.
Figure 24:
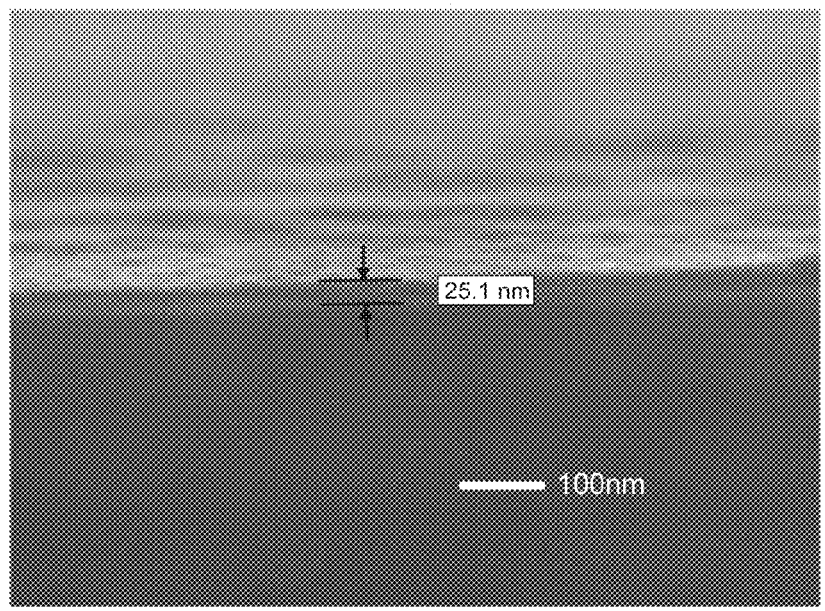
FIG. 24 provides an SEM cross section of a cobalt nitride film deposited by ALD on a Ru/SiO$_2$ substrate at 180° C.
Figure 25:
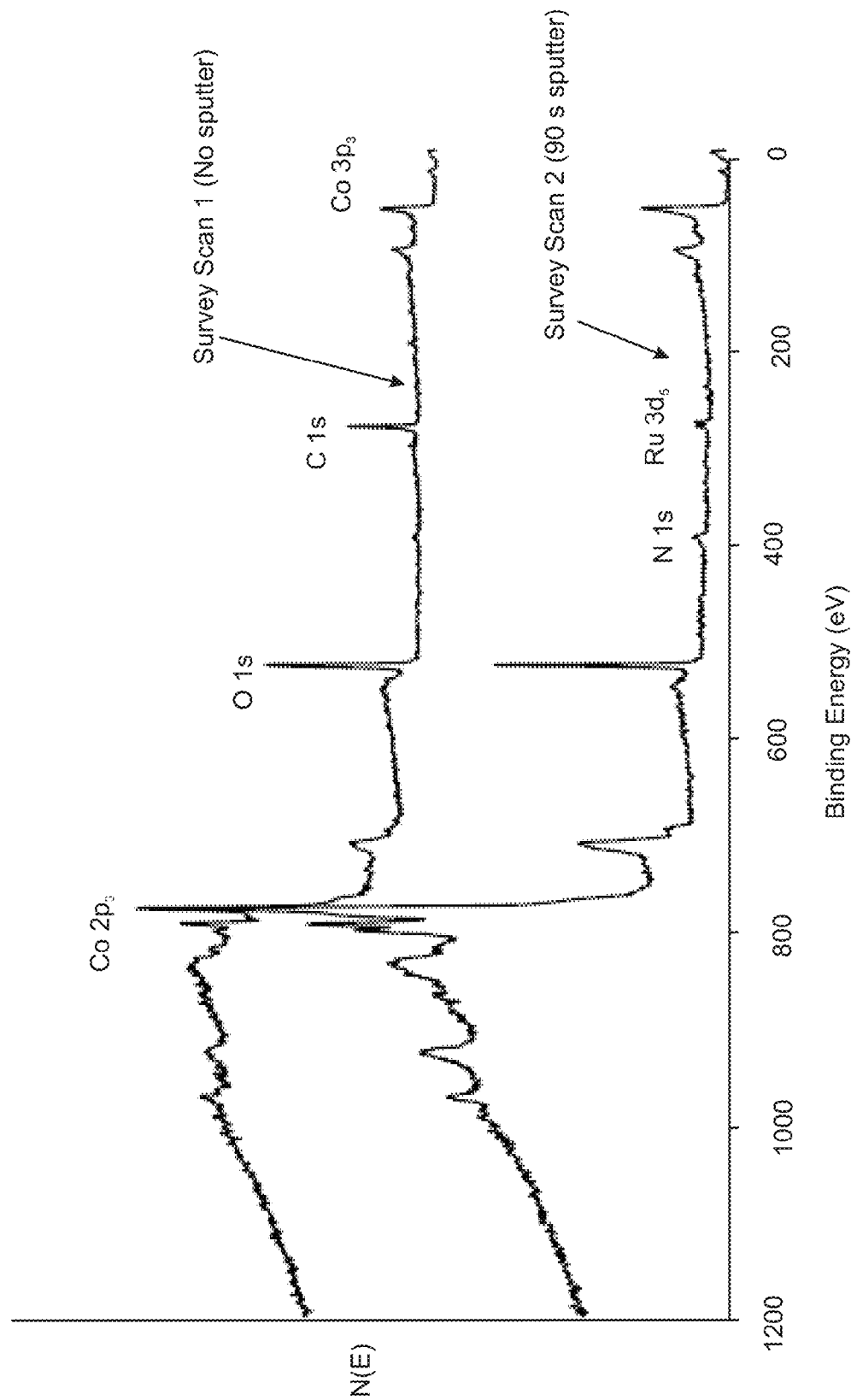
FIG. 25 provides XPS spectrum of a cobalt nitride film deposited by ALD on a Ru/SiO$_2$ substrate at 180° C.
Figure 26:
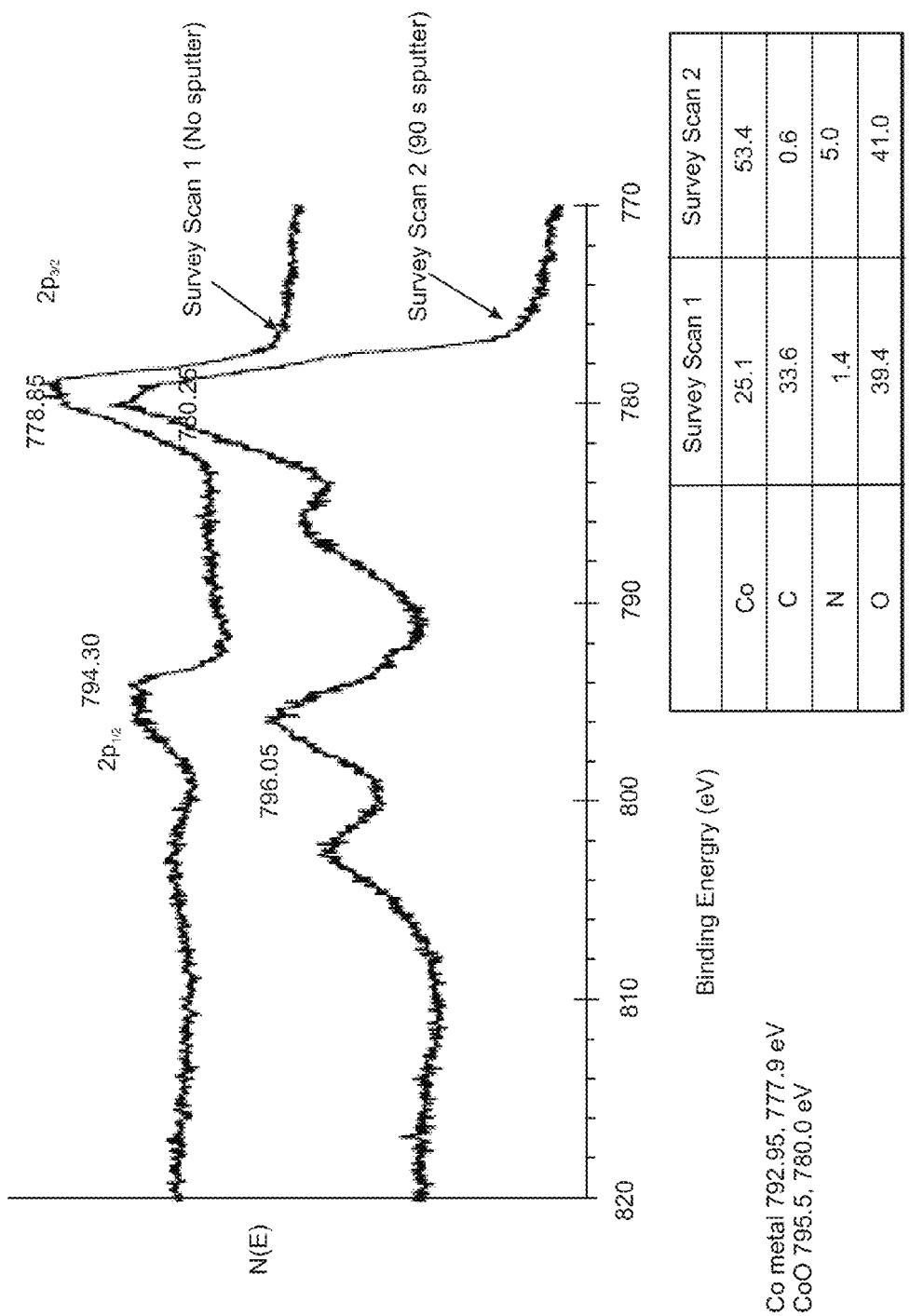
FIG. 26 provides a high resolution multiplexed XPS spectrum of a cobalt nitride film deposited by ALD on a Ru/SiO$_2$ substrate at 180° C.

A cobalt-containing film was deposited in accordance with the following conditions. In a nucleation cycle, 50 cycles were run with a Co Precursor pulse time of 20.0 s, a Co Precursor purge time 5.0 s, BH$_3$.NHMe$_2$ pulse time of 1.0 s, and a BH$_3$.NHMe$_2$ purge time 10.0 s. In film growth step, 1000 cycles were run with a Co Precursor pulse time of 3.0 s, Co Precursor purge time 5.0 s, BH$_3$.NHMe$_2$ pulse time of 1.0 s, and a BH$_3$.NHMe$_2$ purge time 10.0 s. Films were deposited on Ru, Pd, Pt, Si substrates with native oxide, and on H-terminated Si substrates with a substrate temperature of about 180° C., a Co precursor temperature of about 130° C., and a borane precursor temperature of about 80° C. The films on Ru/SiO$_2$ were visually gray in color. FIG. 20 provides an SEM image of the deposited film. Typically, the films have a thickness of about 17 nm. FIGS. 21 and 22 provide XPS spectra confirming that the deposited film is cobalt metal 6. ALD Studies of 8 [Co(iPrMeCOCNtBu)2] with Hydrazine A cobalt-containing film was deposited in accordance with the following conditions. In film growth step, 1000 cycles were run with a Co precursor pulse time of 3.0 s, Co precursor purge time 5.0 s, N$_2$H$_4$ pulse time of 0.4 s, and N$_2$H$_4$ purge time 5.0 s. Films were deposited on Ru, Pd, Pt, Si substrates with native oxide, and on H-terminated Si substrates with a substrate temperature of about 180° C. and a Co precursor 130° C. The films on Ru/SiO$_2$ were visually gray in color. FIGS. 23 and 24 provide SEM images of the deposited film. The film is determined to have a thickness of about 20 nm. FIGS. 25 and 26 provide XPS spectra confirming that the deposited film is cobalt nitride.

Cu/Mn Alloy Deposition

Figure 27:
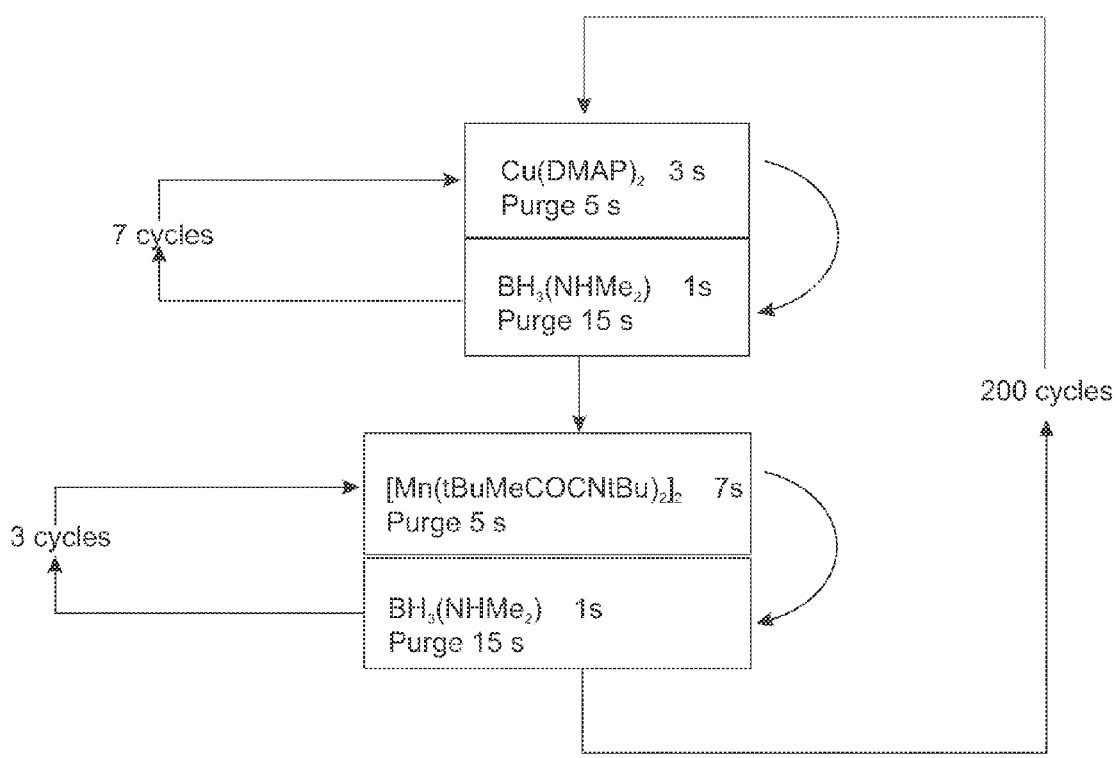
FIG. 27 provides a schematic of the atomic layer deposition of Cu/Mn alloy.

Atomic layer deposition of Cu/Mn alloy was carried out using Cu(DMAP)$_2$ and [Mn(tBuMeCOCNtBu)$_2$]$_2$ as metal precursors and BH$_3$(NMe$_2$) as the reducing agent (coreagent). Cu and Mn precursors were delivered in 7:3 ratios as set forth in FIG. 27. Substrate temperature was 160° C. Visual copper colored films were seen on Ru and Co substrates. Slight copper colored film was seen on silicon with native oxide substrate. Compositional analyses of the surface of these films were analyzed by EDAX equipped with FE-SEM. EDAX analyses reveal that Cu to Mn ratios are approximately 3 to 1 of films grown on Ru and Co and 2 to 1 on silicon with native oxide. By changing the delivery ratio of Cu and Mn precursors, ratios of Cu and Mn may be able to change.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for forming a metal-containing film, the method comprising contacting a compound having formula I with an activating agent to form the metal-containing film:

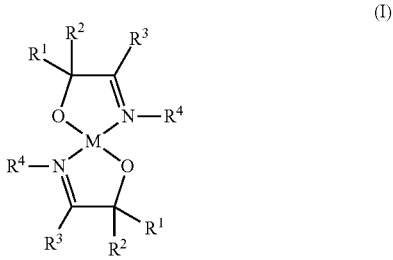

(I)

wherein
  M is a metal selected from Groups 2 to 12 of the Periodic Table; and
  R$^1$, R$^2$, R$^3$, and R$^4$ are each independently H or C$_1$-C$_8$ alkyl.

2. The method of claim 1 wherein the activating agent is a reducing agent.

3. The method of claim 2 wherein the reducing agent is selected from the group consisting of NH$_2$NMe$_2$, NH$_2$NH$_2$, AlEt$_3$, AlMe$_3$, HSiEt$_3$, LiBHEt$_3$, LiAlH$_4$, BH$_3$·N(C$_2$H$_5$)$_3$, BH$_3$·NH(CH$_3$)$_2$, pinacol borane, BH$_3$·S(CH$_3$)$_2$, BH$_3$·THF, BH$_3$·2-picoline, decaborane, 9-Borabicyclo[3.3.1]nonane (9-BBN), BH$_3$·morpholine, and combinations thereof.

4. The method of claim 1 wherein the activating agent is an oxidizing agent or a nitriding agent.

5. The method of claim 1 wherein M is Cu, Cr, Mn, Fe, Co, or Ni.

6. The method of claim 1 wherein R$^1$, R$^2$, R$^3$, and R$^4$ are each independently methyl, ethyl, n-propyl, isopropyl, n-butyl, sec-butyl, isobutyl, or t-butyl.

7. The method of claim 6 wherein a substrate is contacted with a vapor of the compound having formula (I) to form a modified substrate surface during a first deposition cycle.

8. The method of claim 7 further comprising contacting the modified surface with a reducing agent to form a metal film disposed over the substrate during the first deposition cycle.

9. The method of claim 8 wherein the substrate is additionally contacted with the vapor of the compound having formula (I) and then the vapor of a reducing agent during a plurality of additional deposition cycles.

10. The method of claim 9 wherein the substrate is coated with from 1 to 5000 deposition cycles.

11. The method of claim 10 wherein the substrate is coated at a temperature from about 50 to 400° C.

12. The method of claim 11 wherein the substrate is contacted with a purge gas after contacting the substrate with the vapor of the compound having formula (I) and before contacting the substrate with the vapor of the reducing agent.

13. The method of claim 12 wherein the substrate is contacted with the purge gas after contacting the substrate with the vapor of the reducing agent and before a subsequent step of contacting the vapor of the compound.

14. The method of claim 1 wherein the compound having formula (I) is selected from the group consisting of bis(1-(tert-butylimino)-2,3,3-trimethylbutan-2-olate)nickel(II), bis(1-(tert-butylimino)-2,3,3-trimethylbutan-2-olate)cobalt (II), bis(1-(tert-butylimino)-2,3,3-trimethylbutan-2-olate) iron(II), bis(1-(tert-butylimino)-2,3,3-trimethylbutan-2-olate)manganese(II), bis(1-(tert-butylimino)-2,3,3-trimethylbutan-2-olate)chromium(II)(5), bis(1-(tert-butylimino)-2,3,3-trimethylbutan-2-olate)copper(II), bis(1-(tert-butylimino)-2,3-dimethylbutan-2-olate)nickel(II), bis (1-(tert-butylimino)-2,3-dimethylbutan-2-olate)cobalt(II), bis(1-(tert-butylimino)-2,3-dimethylbutan-2-olate)iron(II), bis(1-(tert-butylimino)-2,3-dimethylbutan-2-olate)copper (II), bis(3-((tert-butylimino)methyl)-2,2,4,4-tetramethylpentan-3-olate)manganese(II), bis(3-((tert-butylimino) methyl)-2,2,4,4-tetramethylpentan-3-olate)copper(II), bis (3-(isopropylimino)-2-methylbutan-2-olate)nickel(II), bis (3-(isopropylimino)-2-methylbutan-2-olate)cobalt(II), bis (3-(isopropylimino)-2-methylbutan-2-olate)iron(II), bis(3-(isopropylimino)-2-methylbutan-2-olate)manganese(II), bis (3-(isopropylimino)-2-methylbutan-2-olate)chromium(II) bis(3-(isopropylimino)-2-methylbutan-2-olate)chromium (II), and bis(3-(isopropylimino)-2-methylbutan-2-olate)copper(II).

15. A method of forming a metal film on a substrate, the method comprising a deposition cycle including:
a) contacting a substrate with a vapor of a metal-containing compound described by formula I for a first predetermined pulse time to form a first modified surface:

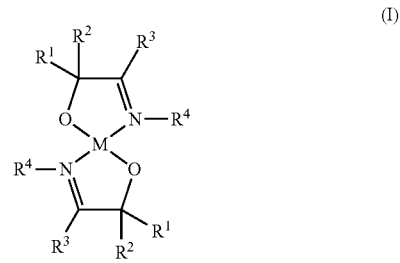

(I)

wherein:
M is a metal selected from Groups 2 to 12 of the Periodic Table; and
R$^1$, R$^2$, R$^3$, and R$^4$ are each independently H or C$_1$-C$_8$ alkyl;
b) contacting the first modified surface with an acid for a second predetermined pulse time to form a second modified surface; and
c) contacting the second modified surface with an activating agent for a third predetermined pulse time to form a metal layer.

16. The method of claim 15 wherein the substrate is subject to a nucleation cycle prior to step a).

17. The method of claim 16 wherein the nucleation cycle comprises contacting the substrate with the vapor of the metal-containing compound described by formula I for a predetermined nucleation pulse time that is greater than the first predetermined pulse time and contacting the substrate with the vapor of the activating agent.

18. The method of claim 16 wherein the nucleation cycle comprises:
contacting the substrate with formic acid;
contacting the substrate with the vapor of the metal-containing compound described by formula I for a predetermined nucleation pulse time that is greater than the first predetermined pulse time; and
contacting the substrate with the vapor of the activating agent.

* * * * *